US009428544B2

(12) United States Patent
Sato et al.

(10) Patent No.: US 9,428,544 B2
(45) Date of Patent: Aug. 30, 2016

(54) METHOD FOR PURIFYING PROTEIN

(71) Applicant: ASAHI KASEI CHEMICALS CORPORATION, Tokyo (JP)

(72) Inventors: Yuta Sato, Tokyo (JP); Naoyuki Shinohara, Tokyo (JP); Hironobu Shirataki, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/347,903

(22) PCT Filed: Sep. 28, 2012

(86) PCT No.: PCT/JP2012/075049
§ 371 (c)(1),
(2) Date: Mar. 27, 2014

(87) PCT Pub. No.: WO2013/047731
PCT Pub. Date: Apr. 4, 2013

(65) Prior Publication Data
US 2014/0235837 A1  Aug. 21, 2014

(30) Foreign Application Priority Data

Sep. 30, 2011 (JP) ................................. 2011-217856

(51) Int. Cl.
| *C07K 1/14* | (2006.01) |
| *C07K 1/16* | (2006.01) |
| *C07K 1/18* | (2006.01) |
| *C07K 1/22* | (2006.01) |
| *B01J 39/04* | (2006.01) |
| *B01J 41/04* | (2006.01) |
| *B01J 47/12* | (2006.01) |

(52) U.S. Cl.
CPC ............. *C07K 1/145* (2013.01); *B01J 39/046* (2013.01); *B01J 41/046* (2013.01); *B01J 47/12* (2013.01); *C07K 1/14* (2013.01); *C07K 1/16* (2013.01); *C07K 1/18* (2013.01); *C07K 1/22* (2013.01)

(58) Field of Classification Search
None
See application file for complete search history.

(56) References Cited

U.S. PATENT DOCUMENTS

| 4,720,343 | A |   | 1/1988 | Walch et al. |
| 5,547,575 | A |   | 8/1996 | Demmer et al. |
| 6,235,892 | B1 | * | 5/2001 | Demmer et al. ............. 536/25.4 |
| 6,780,327 | B1 | * | 8/2004 | Wu et al. ....................... 210/660 |
| 2009/0050566 | A1 |   | 2/2009 | Kozlov et al. |
| 2010/0228010 | A1 | * | 9/2010 | Shirataki et al. .............. 530/413 |

FOREIGN PATENT DOCUMENTS

| EP | 0868932 | * | 7/1998 | ............. B01D 15/08 |
| EP | 0868932 | A2 | 10/1998 | |
| EP | 2226331 | A1 | 9/2010 | |
| JP | 2006-519273 | A | 8/2006 | |
| JP | 2009-053191 | A | 3/2009 | |
| JP | WO/2009/054226 | * | 4/2009 | ............... C07K 1/14 |
| JP | 2011-016119 | A | 1/2011 | |
| WO | 2004-073843 | A | 9/2004 | |
| WO | 2009-054226 | A | 4/2009 | |

OTHER PUBLICATIONS

Koguma et al., Biotechnol. Prog. (2000) 16, 456-461.*
European Search Report for the Application No. 12837457.6, mail date is Jan. 29, 2015.
Pete Gagnon, "17, Polishing Methods for Monoclonal IgG Purification", Process Scale Bioseparations for the Biopharmaceutical Industry, Taylor & Francis Group, LLC, 2007, pp. 491-505.
Kyoichi Saito, Charged Polymer Brush Grafted Onto Porous Hollow-Fiber Membrane Improves Separation and Reaction in Biotechnology, Separation Science, and Technology, England, Taylar & Francis, 2002, 37(3), 535-554.
International Search Report issued with respect to application PCT/JP2012/075049, mail date is Dec. 18, 2012.
International Preliminary Report on Patentability issued with respect to application PCT/JP2012/075049, mail date is Apr. 1, 2014.

* cited by examiner

*Primary Examiner* — Marcela M Cordero Garcia
*Assistant Examiner* — Catherine Mader
(74) *Attorney, Agent, or Firm* — Greenblum & Bernstein, P.L.C.

(57) ABSTRACT

It is an object of the present invention to provide a method for eluting an adsorbed protein that suppresses a decrease in protein adsorption ability, in a method for purifying a protein using a protein-adsorbing porous membrane.
The present invention provides a method for purifying a protein, comprising an adsorption step and an elution step, wherein in the elution step, at least one eluent is passed in the opposite direction with respect to the direction of the passage of a stock solution containing an adsorption target protein, in the adsorption step.

16 Claims, No Drawings

METHOD FOR PURIFYING PROTEIN

TECHNICAL FIELD

The present invention relates to a method for purifying a protein by a porous membrane having a substrate surface coated with a polymer having protein adsorption ability.

BACKGROUND ART

In recent years, in the biotechnology industry, the establishment of a technique that can efficiently mass-produce and mass-purify a protein has been desired.

Generally, a protein is produced by culture using a cell strain derived from an animal or a bacterial cell, such as *Escherichia coli*. Therefore, it is necessary to separate a desired protein from a culture solution and purify the desired protein. Particularly, in order to put a drug utilizing an antibody (antibody drug) to practical use, it is necessary to remove turbid components, such as cell debris, and non-turbid components, such as dissolved proteins derived from cells, from a cell culture solution and purify to purity sufficient for human treatment applications. In the purification step, a protein-adsorbing material, such as a protein-adsorbing porous membrane or beads (particulate adsorption material), is used.

Examples of such a protein-adsorbing material include protein-adsorbing porous membranes as described in Patent Literatures 1 to 5 and Non Patent Literature 1.

Recently, demand for antibody drugs has increased rapidly, and the mass production of proteins that become antibody drugs has been demanded. With rapid progress in culture technique, an improvement in the ability of the purification step has also become a problem. Particularly, an improvement in the ability of protein-adsorbing porous membranes capable of high flow rate treatment has been expected.

CITATION LIST

Patent Literature

Patent Literature 1: International Publication No. WO 2009/054226
Patent Literature 2: Japanese Patent Laid-Open No. 2009-53191
Patent Literature 3: National Publication of International Patent Application No. 2006-519273
Patent Literature 4: U.S. Pat. No. 6,780,327
Patent Literature 5: U.S. Pat. No. 5,547,575

Non Patent Literature

Non Patent Literature 1: Kyoichi Saito, CHARGED POLYMER BRUSH GRAFTED ONTO POROUS HOLLOW-FIBER MEMBRANE IMPROVES SEPARATION AND REACTION IN BIOTECHNOLOGY, Separation Science and Technology, ENGLAND, Taylar & Francis, 2002, 37(3), 535-554

SUMMARY OF INVENTION

Technical Problem

Generally, a protein-adsorbing porous membrane is discarded after a stock solution containing an adsorption target protein (hereinafter sometimes described as a "stock solution") is passed through the protein-adsorbing porous membrane to adsorb the protein, and then, the adsorbed protein is eluted to achieve a purification purpose. But, for the purpose of an improvement in the ability of the purification step, repeated use is required.

When a protein-adsorbing porous membrane is regenerated by treatment of a conventional technique and repeatedly used, the adsorption ability tends to decrease gradually.

In addition, as described above, in recent years, because of demand for mass production and mass purification, it has been desired to make the adsorption ability of protein-adsorbing porous membranes greater. As the method for increasing the adsorption ability, a method of adsorbing a protein on limited membrane pore surfaces in multiple layers is effective. But as a larger amount of a protein is adsorbed on limited membrane pore surfaces in multiple layers, the problem of a decrease in adsorption ability in regenerating the protein-adsorbing porous membrane and repeatedly using it becomes more significant.

Solution to Problem

One of the causes of the decrease in adsorption ability is that not all the adsorbed protein is completely eluted. Therefore, when the efficiency of the elution of the adsorbed protein can be increased, the decrease in adsorption ability due to regenerating the protein-adsorbing porous membrane and repeatedly using it can be suppressed.

The present inventors have studied diligently in order to solve the above problem, and, as a result, found that the above problem can be solved by passing at least one eluent in the opposite direction with respect to the direction of the passage of a stock solution containing an adsorption target protein, in an adsorption step, and completed the present invention. In addition, the present inventors have found that with a protein-adsorbing porous membrane that adsorbs a protein in multiple layers, the above means acts more effectively, and completed the present invention.

Specifically, the present invention is as follows.

[1] A method for purifying a protein by a porous membrane having a substrate surface coated with a polymer having protein adsorption ability, comprising:
an adsorption step of passing a stock solution containing an adsorption target protein through the porous membrane to allow the polymer to adsorb the adsorption target protein; and
an elution step of passing an eluent through the porous membrane to allow the adsorption target protein that is adsorbed on the polymer to elute in the eluent,
wherein in the elution step, at least one eluent is passed in an opposite direction with respect to a direction of passage of the stock solution in the adsorption step.

[2] The method for purifying a protein according to [1], wherein the eluent is selected from the group consisting of an aqueous solution comprising a salt, an aqueous solution whose pH is adjusted, water, an organic solvent, and a mixed solution thereof.

[3] The method for purifying a protein according to [1] or [2], wherein in the elution step, the eluent is passed in a forward direction and an opposite direction with respect to the direction of the passage of the stock solution in the adsorption step.

[4] The method for purifying a protein according to any of [1] to [3], wherein the polymer is grafted onto the substrate surface, and a degree of grafting of the polymer is 5% or more and 200% or less.

[5] The method for purifying a protein according to [4], wherein the degree of grafting of the polymer is 30% or more and 90% or less.

[6] The method for purifying a protein according to any of [1] to [5], wherein the porous membrane is an ion exchange membrane, and the eluent comprises an aqueous solution comprising a salt or an aqueous solution whose pH is adjusted.

[7] The method for purifying a protein according to any of [1] to [6], wherein a degree of multilayering of the porous membrane is 1.1 or more.

[8] The method for purifying a protein according to [6] or [7], wherein the porous membrane is a weakly basic anion exchange membrane or a weakly acidic cation exchange membrane, the elution step comprises the steps of:

passing an aqueous solution whose pH is adjusted to other than between an isoelectric point of the adsorption target protein and an isoelectric point of the porous membrane, and passing an aqueous solution comprising a salt, wherein in either of the steps, the aqueous solution whose pH is adjusted or the aqueous solution comprising a salt is passed in the opposite direction with respect to the direction of the passage of the stock solution in the adsorption step.

[9] The method for purifying a protein according to [8], wherein in the step of passing an aqueous solution whose pH is adjusted, and the step of passing an aqueous solution comprising a salt, respectively, the aqueous solution whose pH is adjusted and the aqueous solution comprising a salt are passed in the opposite direction with respect to the direction of the passage of the stock solution in the adsorption step.

[10] The method for purifying a protein according to [6] or [7], wherein the porous membrane is a weakly basic anion exchange membrane or a weakly acidic cation exchange membrane, the elution step comprises a first step of passing an aqueous solution comprising a salt, a second step of passing an aqueous solution whose pH is adjusted to other than between an isoelectric point of the adsorption target protein and an isoelectric point of the porous membrane, and a third step of passing an aqueous solution comprising a salt, in the first step, the aqueous solution comprising a salt is passed in the forward direction with respect to the direction of the passage of the stock solution in the adsorption step, and in the second step and the third step, respectively, the aqueous solution whose pH is adjusted and the aqueous solution comprising a salt are passed in the opposite direction with respect to the direction of the passage of the stock solution in the adsorption step.

[11] The method for purifying a protein according to any of [1] to [10], wherein the eluent is adjusted at a stable pH for the adsorption target protein.

[12] The method for purifying a protein according to any of [1] to [11], wherein the eluent is an aqueous solution comprising a neutral salt at 0.3 mol/L or more.

[13] The method for purifying a protein according to any of [1] to [12], wherein the porous membrane is manufactured by performing treatment of heating to 50 to 110° C. in a state of being wetted with a liquid or a vapor.

Advantageous Effect of Invention

The present invention can provide a method for eluting an adsorbed protein that suppresses a decrease in protein adsorption ability, in a method for purifying a protein using a protein-adsorbing porous membrane.

DESCRIPTION OF EMBODIMENT

A preferred embodiment of the present invention will be described in detail below. However, the present invention is not limited to the following embodiment, and various modifications can be made without departing from the spirit thereof.

A method for purifying a protein in this embodiment is a method comprising an adsorption step and an elution step, wherein in the elution step, at least one eluent is passed in the opposite direction with respect to the direction of the passage of a stock solution containing an adsorption target protein in the adsorption step.

The porous membrane used in this embodiment is a membrane comprising a substrate and a polymer having protein adsorption ability coating the surface of the substrate, and is sometimes described as a "protein-adsorbing porous membrane."

In this embodiment, the "protein-adsorbing porous membrane" is used as a concept also including a form referred to as a monolith in which a cylindrical porous sintered body having one or a plurality of hollow portions is coated with a polymer having protein adsorption ability. Therefore, in this embodiment, a "porous membrane having a substrate surface coated with a polymer having protein adsorption ability" also includes a monolith (hollow cylindrical porous sintered body) having a surface coated with a polymer having protein adsorption ability.

In this embodiment, by illustration by the description "protein-adsorbing porous membrane," a monolith (hollow cylindrical porous sintered body) coated with such a polymer is also included in the range of its substance.

In this embodiment, by passing the stock solution containing an adsorption target protein through the protein-adsorbing porous membrane, the adsorption target protein is adsorbed on the protein-adsorbing porous membrane. The stock solution containing an adsorption target protein is a solution comprising a protein to be adsorbed on the protein-adsorbing porous membrane and means a solution before passing through the membrane.

In this embodiment, a solution after passing through the membrane is described as a "passed solution."

Usually, in an actual manufacturing line in manufacturing a drug, in addition to a desired protein, waste proteins, bacterial cells, viruses, turbid components, and the like are contained in a stock solution. The turbid components and/or the bacterial cells can be removed from the stock solution by pretreatment. In this embodiment, a purification method involving adsorbing a desired protein on the protein-adsorbing porous membrane as an adsorption target substance and allowing other components to permeate, and then eluting only the desired protein and recovering it may be used, or a purification method of adsorbing other proteins (for example, waste proteins) as adsorption target substances and allowing a desired protein to permeate and recovering it may be used. In other words, the "adsorption target protein" is a protein to be adsorbed on the protein-adsorbing porous membrane and is not limited to a desired protein. The "adsorption target protein" may be a desired protein or waste proteins according to the purification method. In addition, the adsorption target protein contained in the stock solution may be one or more.

In this embodiment, the "adsorption" means that a protein sticks by interaction with the pore surfaces of the protein-adsorbing porous membrane, and is distinguished from "adhesion," which is only simple contact.

In this embodiment, the step of passing a stock solution containing an adsorption target protein through a porous membrane to adsorb the adsorption target protein is sometimes described as an "adsorption step."

Subsequently, the step of washing away components "adhering" to the protein-adsorbing porous membrane (that is, proteins that are not a target of adsorption (non-adsorbed proteins) and turbid components) can be performed. This step is described as a "washing step" and distinguished from the "elution step" described later. By the washing step, the "adsorbed" protein is present on the protein-adsorbing porous membrane surface.

Finally, the adsorbed protein adsorbed on the protein-adsorbing porous membrane is eluted from the protein-adsorbing porous membrane with the eluent and recovered. The eluent here is a liquid for eluting the adsorbed protein and is not used as the meaning of a solution that has passed through the protein-adsorbing porous membrane and exited.

In this embodiment, the step of passing the eluent through the protein-adsorbing porous membrane to elute the adsorbed protein from the protein-adsorbing porous membrane is sometimes described as an "elution step."

In this embodiment, the elution step may be the step of passing the eluent not only for eluting the adsorbed protein from the protein-adsorbing porous membrane but for regenerating the protein-adsorbing porous membrane. In other words, the content of the adsorbed protein in the eluent in the elution step is not particularly regarded as a problem.

In the elution step, by passing at least one eluent in the opposite direction with respect to the direction of the passage of the stock solution in the adsorption step, the protein can be purified, and the protein-adsorbing porous membrane can be regenerated.

It can also be said that in this embodiment, in the method for purifying a protein by a porous membrane having a substrate surface coated with a polymer having protein adsorption ability, not only a method involving eluting an adsorbed protein that suppresses a decrease in protein adsorption ability is provided, but a method involving regenerating the protein-adsorbing porous membrane can be provided because the elution of the adsorbed protein is part of the regeneration treatment of the protein-adsorbing porous membrane.

The details of the mechanism in the method for purifying a protein in this embodiment are unclear but can be considered as follows.

Usually, in an elution step, an eluent is passed in the forward direction with respect to the direction of the passage of a stock solution in an adsorption step.

Although not to be bound by the following theory, it is considered that by passing the eluent with the direction of the flow of the eluent changed to the opposite direction with respect to the direction of the passage of the stock solution at least once as in this embodiment, the adsorbed protein can be eluted by the effect of polymer chains having protein adsorption ability introduced into the surface of the substrate in the protein-adsorbing porous membrane being shaken. In other words, the protein can be adsorbed stacked in multiple layers so as to enter between adjacent polymer chains, and the protein that gets in deep is not easily eluted. It is considered that the polymer chains trail in the direction of the flow of the stock solution in the adsorption step. Therefore, it is considered that by flowing the eluent in the opposite direction with respect to the direction of the flow of the stock solution in the elution step, the polymer chains are rubbed the wrong way, and the protein that gets in deep is efficiently eluted, and therefore, the protein-adsorbing porous membrane can be regenerated as a membrane in which a decrease in adsorption ability is suppressed in repeated use.

The purification of a protein can also be performed using as a protein-adsorbing material protein-adsorbing beads, in addition to the protein-adsorbing porous membrane. When the protein-adsorbing beads are used, the purification of a protein is performed in a state in which a cylindrical case (column) is filled with the protein-adsorbing beads. As the regeneration method, the liquid can be flowed through the case in the opposite direction with respect to the direction of the passage of the stock solution, but this is performed for the purpose of removing turbid components and loosening compacted beads. Even if the liquid is flowed through the case in the opposite direction, it is difficult to control the flow of the liquid on the surface of each bead particle, and the movement of the protein in the pore portion leading to the inside from the bead surface is diffusion-controlled. Therefore, the direction of the flow of the liquid through the case does not affect the elution, and it can be said that this embodiment is a regeneration method particularly effective for the protein-adsorbing porous membrane.

Examples of the shape of the protein-adsorbing porous membrane include a flat membrane and a hollow fiber membrane.

The flat membrane is a sheet-shaped membrane and means one in which the front surface and back surface of a sheet are continuous through pores that are through holes.

The hollow fiber membrane is a cylindrical or fibrous membrane having a hollow portion and means one in which the hollow side (inside) and outside of a hollow fiber membrane are continuous through pores that are through holes.

The shape of the protein-adsorbing porous membrane is not particularly limited as long as a liquid or a gas can permeate from the front surface to the back surface or from the back surface to the front surface, and from the inside to the outside or from the outside to the inside, through the through holes.

Usually, a protein-adsorbing porous membrane cannot be effectively used only with the membrane and is used in a state of being housed in a packing container, referred to as a module, in order to perform liquid passage. Because the flow path structure in module molding is simple, and the liquid passage in the opposite direction with respect to the direction of the passage of the stock solution in the adsorption step is easy, the hollow fiber membrane is preferred. The module structure should be a known structure corresponding to the shape of each protein-adsorbing porous membrane and is not particularly limited in this embodiment.

In this embodiment, the dimensions of the protein-adsorbing porous membrane can be freely selected according to the module design, the manufacturing method and use application of the membrane. For example, in the case of a flat membrane, it can be molded into a module, and the thickness and size of the sheet can be freely designed as long as liquid passage is possible. In the case of a hollow fiber membrane or a monolith, the dimensions of the outer diameter and the inner diameter can be freely designed as long as the shape of the porous membrane can be physically retained.

In this embodiment, as the substrate of the protein-adsorbing porous membrane, materials of known techniques can be used as long as they are resistant to the contact liquids used in the purification of the protein.

Examples thereof include polymer materials, inorganic materials, and organic-inorganic hybrid materials. From the viewpoint of moldability, polymer substrates using polymer materials are preferred.

When a polymer substrate is used, the polymer substrate is preferably composed of a polyolefin-based polymer from the viewpoint of retaining mechanical properties.

Examples of the polyolefin-based polymer include homopolymers of olefins, such as ethylene, propylene, and butylene, and copolymers of two or more of the olefins.

When an alkaline solution is used as the eluent, among these, polyethylene, which has particularly excellent mechanical strength and has alkali resistance, is more preferred.

The polymer substrate can be manufactured as a porous membrane by known techniques, such as a thermally induced phase separation method, a non-solvent phase separation method, and an electron beam irradiation method.

The thermally induced phase separation method is a method of melting a solution of a polymer, such as a polyolefin-based polymer, at high temperature and then cooling the solution. In the cooling process, the polymer solution phase-separates into the polymer and the solvent in the form of a network. Therefore, when the solvent is removed after the cooling, a porous membrane is obtained. The thermally induced phase separation method is characterized in that a porous membrane having a small pore diameter distribution is obtained.

The non-solvent phase separation method is a method of immersing a polymer solution in a non-solvent. The non-solvent penetrates into the polymer solution, and thus, the solubility of the polymer decreases, the polymer precipitates in the form of a network, and a porous membrane is obtained. The non-solvent phase separation method is characterized in that a porous membrane having gradient pore diameters is obtained.

The electron beam irradiation method is a method of irradiating a membrane-shaped polymer with an electron beam to make a plurality of through holes to obtain a porous membrane. A porous membrane having a uniform pore diameter is obtained.

In this embodiment, among these methods, an appropriate one can be selected according to the design of the protein-adsorbing porous membrane to be fabricated.

The average pore diameter of the substrate in this embodiment is not particularly limited as long as the degree of separation and purification and liquid passage rate required for the process can be achieved considering the type of the adsorption target protein, the mixed turbid components, the viscosity of the solution, and the like. The upper limit of the average pore diameter is designed so that the turbid components can be removed, and the lower limit of the average pore diameter is designed so that the desired liquid passage rate can be achieved. The average pore diameter is preferably 0.001 µm to 10 µm, more preferably 0.01 µm to 10 µm, and further preferably 0.1 µm to 1 µm.

The porosity that is the volume ratio of the pores in the substrate is not particularly limited as long as it is in a range in which the shape of the protein-adsorbing porous membrane is retained and the liquid passage rate can be achieved. The upper limit of the porosity is designed so that shape retention is possible, and the lower limit of the average pore diameter is designed so that the desired liquid passage rate can be achieved. The porosity is preferably 5% to 99%, more preferably 10% to 95%, and practically further preferably 30 to 90%.

The measurement of the average pore diameter and the porosity can be performed by a method usual for those skilled in the art, for example, as described in Marcel Mulder, "Membrane Technology" (Industrial Publishing & Consulting, Inc.). Specific examples of the measurement method include observation by an electron microscope, a bubble point method, a mercury intrusion method, and a permeability method.

In this embodiment, the surface of the substrate, preferably at least part of the pores, is coated with the polymer having protein adsorption ability.

Examples of the polymer include linear polymers and crosslinked polymers. Because the flow of the eluent in the opposite direction can efficiently elute the protein entering between polymer chains, linear polymers are preferred.

Protein-adsorbing porous membranes are classified into ion exchange membranes, group-specific affinity adsorption membranes, individual-specific affinity adsorption membranes, and hydrophobic interaction adsorption membranes by the functional group of the polymer coating the substrate surface. Ion exchange membranes are finely classified into strongly acidic cation exchange membranes, weakly acidic cation exchange membranes, strongly basic anion exchange membranes, and weakly basic anion exchange membranes.

In this embodiment, for the functional groups of these, appropriate ones can be selected according to the type of the adsorbed protein, preferably the type of the desired protein, the required degree of purification, and the like.

Examples of the functional groups of the strongly acidic cation exchange membranes include a sulfonic acid group ($-SO_3^-$). Examples of the functional groups of the weakly acidic cation exchange membranes include a carboxylic acid group ($-COO^-$).

Examples of the functional groups of the strongly basic anion exchange membranes include quaternary ammonium groups (Q, $-N^+R_3$) and quaternary aminoethyl groups (QAE, $-(CH_2)_2-N^+R_3$). Here, R is not particularly limited, and R bonded to the same N may be the same or different. R preferably represents a hydrocarbon group, such as an alkyl group or an aryl group. More specific examples include a trimethylamino group (TMA, $-N^+Me_3$).

Examples of the functional groups of the weakly basic anion exchange membranes include primary amino groups ($-NH_2$), secondary amino groups ($-NHR$), and tertiary amino groups ($-NR_2$), and specifically a diethylaminoethyl group (DEAF, $-(CH_2)_2-NEt_2$) and a diethylaminopropyl group (DEAP, $-(CH_2)_3-NEt_2$). Also here, R is not particularly limited, and R bonded to the same N may be the same or different. R preferably represents a hydrocarbon group, such as an alkyl group or an aryl group.

Examples of the functional groups of the group-specific affinity adsorption membranes include Cibacron Blue F3G-A, protein A, concanavalin A, heparin, tannin, and metal chelate groups.

Examples of the functional groups of the individual-specific affinity adsorption membranes include antigens and antibodies.

Examples of the functional groups of the hydrophobic interaction adsorption membranes include alkyl groups and aromatic functional groups. The alkyl groups preferably have four or more carbon atoms from the viewpoint of further increasing hydrophobic interaction and increasing adsorption ability.

In this embodiment, examples of the method for introducing into the substrate surface the polymer having protein adsorption ability coating the substrate surface include chemical reactions or polymer application. In this embodiment, an optimal method can be selected from the viewpoint of the material of the substrate, the use application and manufacturing method of the protein-adsorbing porous membrane, and the like and can also be applied to a porous sintered body referred to as a monolith.

Examples of the method for coating the substrate surface with the polymer having protein adsorption ability by a chemical reaction include a radiation graft polymerization method. The radiation graft polymerization method is a method involving irradiating a substrate with radiation, such as γ rays, to activate the substrate surface to polymerize the monomer. Compared with the coating method by polymer application described later, the firm bond between the substrate and the polymer coating the substrate surface can be expected. Further, from the viewpoint that reagents, such as a polymerization initiator, are unnecessary, and therefore, the load of washing these reagents after the reaction can be reduced, the radiation graft polymerization method is preferably used.

The radiation graft polymerization method includes (1) a method involving graft-polymerizing a monomer having a functional group having protein adsorption ability directly onto a substrate, or (2) a method involving graft-polymerizing onto a substrate a monomer comprising a functional group into which a functional group having protein adsorption ability can be introduced and then introducing the functional group having protein adsorption ability. Both can be used.

In this embodiment, a polymer introduced by graft polymerization may be referred to as a "graft chain."

The method shown as the above (1) is a simple and preferred method because a coating layer of a polymer having protein adsorption ability is obtained in a one-step reaction.

The above monomer used in the method of (1) is not particularly limited. Examples of the above monomer include methacrylate derivatives, vinyl compounds, and allyl compounds and specifically, diethylaminoethyl methacrylate, sulfopropyl methacrylate, vinylbenzyltrimethylammonium chloride, and allylamine.

The method shown as the above (2) is a preferred method from the viewpoint of easily having variations of various functional groups having protein adsorption ability or easily having variations in the introduction rate (hereinafter sometimes described as "ligand conversion rate") of the functional group having protein adsorption ability.

The above monomer used in the method of (2) is not particularly limited. Examples of the above monomer include glycidyl methacrylate (GMA) having an epoxy group having high reactivity.

When the polymer having protein adsorption ability is introduced by the radiation graft polymerization method, the amount of the graft chains (hereinafter sometimes described as a "degree of grafting") and the ligand conversion rate can affect the adsorption ability and mechanical strength of the protein-adsorbing porous membrane.

In this embodiment, the degree of grafting (dg [%]) is defined based on the increased weight of the substrate before and after radiation graft polymerization and can be obtained by the following formula (1).

[Expression 1]

$$dg[\%] = \frac{W_1 - W_0}{W_0} \times 100 \qquad (1)$$

$W_0$: substrate weight (g)
$W_1$: weight after radiation graft polymerization (g)

In this embodiment, the ligand conversion rate (T [%]) is defined by the abundance of a functional group having protein adsorption ability to functional groups into which the functional group having protein adsorption ability can be introduced in the graft chain, and can be obtained by the following formula (2).

[Expression 2]

$$T[\%] = \frac{(W_2 - W_1)/M_2}{\{(W_1 - W_0)/M_1\} \times a} \times 100 \qquad (2)$$

$W_0$: substrate weight (g)
$W_1$: weight after radiation graft polymerization (g)
$W_2$: total weight after introduction of functional group having protein adsorption ability (g)
$M_1$: molecular weight of graft chain monomer unit (g/mol)
$M_2$: molecular weight of functional group having protein adsorption ability (g/mol)
$a$: number of functional groups into which the functional group having protein adsorption ability can be introduced per graft chain monomer molecule In the above formula (2), when a graft chain is introduced using GMA as a monomer comprising a functional group into which a functional group having protein adsorption ability can be introduced, $a=1$ holds because the functional group into which the functional group can be introduced is one epoxy group in the monomer.

In this embodiment, the degree of grafting is preferably a higher degree of grafting in order to adsorb a large amount of the protein on limited pore surfaces. However, when the degree of grafting is increased, the graft chain traverses the pore space and comes into contact with the opposed pore surface, and the shake of the graft chain due to changing the direction of liquid passage decreases, and the efficiency of the elution of the adsorbed protein can decrease. Therefore, the degree of grafting is preferably 5% to 200%. In addition, when the graft chain is made larger, the pore space becomes smaller, and therefore, the liquid passage pressure increases, and the desired liquid passage rate cannot be achieved in some cases. Therefore, the degree of grafting is more preferably 20% to 150%. In addition, when the graft chain is made larger, the mechanical strength can also decrease. Therefore, from a practical viewpoint, the degree of grafting is further preferably 30% to 90%.

The ligand conversion rate is preferably 20% to 100%, more preferably 50% to 100%, and further preferably 70% to 100%, from the viewpoint of obtaining higher adsorption capacity.

The ligand introduction is followed by the drying step and module molding step of the protein-adsorbing porous membrane, the manufacturing process. Unless the mechanical strength, adsorption performance, and the like of the protein-adsorbing porous membrane are affected in terms of practical performance, appropriate means can be selected in each step. In addition, additional steps may be appropriately added, and omission may be made.

For example, after the module molding step, the treatment (wet heat treatment) step of heating in a state of being wetted with a liquid or a vapor may be carried out on the protein-adsorbing porous membrane. The adsorption ability can be improved by the wet heat treatment, and therefore, the wet heat treatment is preferably carried out.

The liquid used in the wet heat treatment is preferably pure water or an aqueous solution. The aqueous solution is not particularly limited as long as it is an aqueous solution comprising an inorganic salt. From the viewpoint of the maintenance of the treatment apparatus and the viewpoint of reducing the work load of aqueous solution adjustment, pure water is preferably used.

In addition, the temperature of the wet heat treatment is preferably 50 to 110° C., and is more preferably 60 to 95°

C. from the viewpoint of workability when pure water is used and the effect of the wet heat treatment.

Examples of the method for coating the substrate surface with the polymer having protein adsorption ability by a chemical reaction also include a graft polymerization method using a polymerization initiator. This graft polymerization method is a method involving activating a substrate using a polymerization initiator to polymerize the monomer to introduce a graft chain into the substrate surface. The graft polymerization method is preferably used from the viewpoint that graft polymerization can also be possible for a substrate that is difficult to activate by radiation and the viewpoint that radiation irradiation equipment is unnecessary. For example, when a porous sintered body, such as a monolith, manufactured by a known technique is used as a substrate, the graft polymerization method can be used as a method for coating its surface.

Examples of the method for coating the substrate surface with the polymer having protein adsorption ability by polymer application include a method involving applying a polymer comprising a functional group having protein adsorption ability to a substrate and fixing the polymer to the substrate surface with a crosslinking agent. As such a method, for example, a specific method is disclosed in Patent Literature 4. Other examples include a method involving forming a coating of a polymer or a polymer precursor on a substrate surface and obtaining a new graft polymer using the polymer constituting the coating as a polymerization start point. As such a method, for example, a specific method is disclosed in Patent Literature 5.

Examples of the protein-adsorbing porous membrane to which the method for purifying a protein in this embodiment can be applied include membranes described in Patent Literatures 1 to 5.

Patent Literature 1 shows a porous membrane having on a pore surface a graft chain to which an anion exchange group is fixed. It is reported that a protein is adsorbed in multiple layers on a porous hollow fiber membrane similar to that of Patent Literature 1 in which a polymer brush (linear graft chains) having an ion exchange group is introduced into a pore surface (Non Patent Literature 1).

In other words, it can be said that the membrane described in Patent Literature 1 is a membrane on which the present purification method in which an eluent is flowed in the opposite direction to rub polymer chains the wrong way to efficiently elute an adsorbed protein acts particularly effectively.

Patent Literature 2 shows a porous adsorption medium in which a porous substrate is covered with an adsorption material having a crosslinked polymer to which a primary amine group is bonded. For the coating polymer covering the substrate, it is described that "proteins and other impurities are captured deep in the coating." It can be said that the membrane described in Patent Literature 2 is a membrane on which the present purification method acts effectively.

Patent Literature 3 shows a composite material comprising a support-constituting member in which a plurality of holes extends and a macroporous crosslinked gel disposed in the holes of the support-constituting member and filling the holes of the support-constituting member.

Patent Literature 4 shows a positively charged porous membrane comprising a crosslinked film having a cation functional group (meaning an "anion exchange functional group" in this embodiment) and a porous substrate. As one example of the manufacturing method, for example, the following method is shown. First, a reagent having an epoxy group (for example, epichlorohydrin) is added to a copolymer of diallylamine and a methacrylate derivative having a quaternary ammonium functional group for activation. A crosslinking agent comprising pentaethylenehexamine and glycidyltrimethylammonium chloride is separately formulated. Then, a porous membrane that is a substrate is immersed in a solution of the activated copolymer and the crosslinking agent to obtain a protein-adsorbing membrane.

Patent Literature 5 shows a membrane obtained by forming a coating of an N-halogenated compound (polymer or polymer precursor) on a polymer porous substrate membrane surface and bringing a graft initiator and a monomer into contact for graft polymerization on the substrate. As a specific example, a membrane that is obtained by graft polymerization on a porous membrane made of cellulose using N-halogenated nylon 66 as the above N-halogenated compound and using GMA as the above monomer followed by the sulfonation of the epoxy group by treatment with sulfonate ions is mentioned. In addition, a membrane in which a tertiary amino group/quaternary ammonium group from a secondary/tertiary amine is introduced into the epoxy group of GMA is described.

These membranes disclosed in Patent Literatures 1 to 5 and Non Patent Literature 1 are mentioned as illustrations of protein-adsorbing porous membranes that can be preferably used in the method for purifying a protein by a protein-adsorbing porous membrane in this embodiment.

In this embodiment, the degree of multilayering is an indicator representing the adsorbed form of the adsorbed protein on the limited pore surfaces of the protein-adsorbing porous membrane. When a protein is adsorbed on the pore surface of a protein-adsorbing porous membrane, there are single-layer adsorption in which the protein is placed on the pore surface and multilayer adsorption in which another protein is further laminated and adsorbed on the adsorbed protein. The structure of the polymer having protein adsorption ability on the pore surfaces of the protein-adsorbing porous membrane affects the adsorbed form of the adsorbed protein, and therefore, it can be said that the degree of multilayering is an indicator indirectly indicating the polymer structure on the pore surfaces. The degree of multilayering in this embodiment is taken as the number of layers in terms of BSA (bovine serum albumin) when a protein is adsorbed on the pore surfaces of the protein-adsorbing porous membrane to the amount of equilibrium adsorption with the closest packing. In other words, the number of laminated layers when the amount of equilibrium adsorption is measured with an arbitrary protein and the particle size of the arbitrary protein used for the measurement is converted to that of BSA is the degree of multilayering and is an indicator that can compare the polymer structure on the pore surfaces also when measurement is performed using a protein having an arbitrary size according to the protein-adsorbing porous membrane to be evaluated.

The concept of the degree of multilayering itself appears as the degree of multilayer binding of protein, for example, in Non Patent Literature 1, and is a concept known to those skilled in the art.

In this embodiment, the degree of multilayering is a value obtained by the following formula (3).

[Expression 3]

$$\text{degree of multilayering} = (\text{equilibrium adsorption capacity})/(\text{theoretical single-layer adsorption capacity}) \quad (3)$$

The "equilibrium adsorption capacity" is widely used in the industry as a term representing the adsorption ability of a protein-adsorbing porous membrane. The "equilibrium adsorption capacity" refers to adsorption capacity until a point at which, when a stock solution comprising an adsorption target protein is passed through a protein-adsorbing porous membrane, the protein concentration in the passed solution of the stock solution reaches equilibrium with the concentration of the protein in the stock solution (adsorption equilibrium), and is obtained by the following formula (4).

The "adsorption capacity" means a numerical value obtained by converting the amount of adsorption to a value per unit amount of a membrane. The "amount of adsorption" means the weight of an adsorbed protein adsorbed by a protein-adsorbing porous membrane.

When adsorption capacity is evaluated, it is generally evaluated with a stock solution of a solution of a purified protein unlike the case of use in an actual manufacturing line.

[Expression 4]

$$\text{equilibrium adsorption capacity} \left[ \frac{g - \text{amount of adsorption}/}{g - \text{membrane}} \right] = \frac{\int_0^{Q_e}(C_0 - C)dQ}{W} \quad (4)$$

$C_0$: concentration of protein in stock solution [g/L]
$C$: protein concentration in passed solution of stock solution [g/L]
$Q$: cumulative amount of passed solution of stock solution [L]
$Q_e$: amount of passed solution of stock solution when adsorption equilibrium is reached [L]
$W$: weight of protein-adsorbing porous membrane [g]

The measurement of equilibrium adsorption capacity is performed using a commercial experimental protein, and this is converted to the degree of multilayering of BSA protein (described in detail later). The protein used for the measurement can be arbitrarily selected according to the protein-adsorbing porous membrane. For example, for a strongly basic anion exchange membrane and a weakly basic anion exchange membrane, BSA is preferably used. On the other hand, for a strongly acidic cation exchange membrane and a weakly acidic cation exchange membrane, lysozyme is preferably used.

The pH of the protein solution used for the evaluation should be in a pH region in which the protein is adsorbed on the protein-adsorbing porous membrane and the protein does not denature and is stable. For example, in the case of an ion exchange membrane, a stock solution comprising a protein adjusted to a pH between the isoelectric point (pI) of the protein and the pI of the ion exchange membrane is used. The relationship between the pI of the protein and the pI of the ion exchange membrane will be described in detail later.

The "theoretical single-layer adsorption capacity" is obtained by dividing the specific surface area of a protein-adsorbing porous membrane by the area occupied by one protein molecule to calculate the number of proteins theoretically arranged closest on the surface, and using the following formula (5) using Avogadro's number ($N_A$) and the molecular weight of the protein ($M_r$).

[Expression 5]

$$\text{theoretical single-layer adsorption capacity}[g-\text{amount of single-layer adsorption}/g-\text{membrane}] = (S_M/S_P)(M_r/N_A) \quad (5)$$

$S_M$: specific surface area of protein-adsorbing porous membrane [m$^2$/g]
$S_P$: area occupied by one protein molecule [m$^2$]
$M_r$: molecular weight of BSA [g/mol]
$N_A$: Avogadro's number [/mol]

In this embodiment, as described above, the degree of multilayering is taken as the number of laminated layers in terms of BSA. Therefore, the theoretical single-layer adsorption capacity is taken as the theoretical single-layer adsorption capacity in terms of BSA. In other words, in formula (5), for the area occupied by one protein molecule $S_P$, $S_P$=4.0 nm×4.0 nm=16 nm$^2$ is used from the particle size of BSA (4.0 nm×4.0 nm×11.5 nm), and for the molecular weight $M_r$, 67500 is used.

The specific surface area of the protein-adsorbing porous membrane $S_M$ can be measured by a nitrogen adsorption method (BET method).

For the degree of multilayering, the ease of trailing of the polymer chains on the pore surfaces of the protein-adsorbing porous membrane (that is, the magnitude of the effect of elution) is preferably larger. However, by an increase in the degree of multilayering, the liquid passage pressure increases, and the desired liquid passage rate becomes difficult to achieve. Therefore, the degree of multilayering is preferably 15 or less, and the degree of multilayering is more preferably 1.1 to 15, further preferably 2 to 15, and still further preferably 3 to 15.

In this embodiment, the adsorption step can be carried out as in a purification method using a general protein-adsorbing porous membrane and is performed by the procedure of (1-1) the equilibration of the protein-adsorbing porous membrane with a buffer and (1-2) protein adsorption on the protein-adsorbing porous membrane by the passage of a stock solution containing an adsorption target protein.

The above (1-1) step is the step of passing a buffer to equilibrate the state (charge state or the like) of the polymer having a protein adsorption function, and is performed as a protein adsorption preparation procedure.

The above (1-2) step is the step of passing through the equilibrated protein-adsorbing porous membrane a stock solution containing an adsorption target protein, to adsorb on the protein-adsorbing porous membrane the adsorption target protein, and is performed as an essential procedure as the adsorption step in this embodiment.

In the (1-2) step, the adsorption target protein is appropriately selected. A method of adsorbing a desired protein and subsequently eluting and recovering it, and a method of adsorbing waste proteins and passing a desired protein and recovering it are mentioned.

The buffer used in this embodiment is not particularly limited as long as a suitable one is selected according to the purification process, the type of the adsorption target protein, and the type of the functional group having protein adsorption ability (a hydrophobic interaction membrane, an ion exchange membrane, a group-specific affinity adsorption membrane, or an individual-specific affinity adsorption membrane). The buffer can be appropriately selected. Examples of the buffer include a hydrochloric acid-potassium chloride buffer, a glycine-hydrochloric acid buffer, a citrate buffer, an acetate buffer, a citrate-phosphate buffer, a phosphate buffer, a tris-hydrochloric acid buffer, and a glycine-sodium hydroxide buffer. A suitable one can be selected according to the adsorption target protein and the purification process.

In this embodiment, the molecular weight of the adsorption target protein can be arbitrarily selected as long as the protein can be adsorbed on the pore surfaces of the protein-adsorbing porous membrane. The molecular weight should be a molecular size in which the protein can be eluted with the eluent, has a pore diameter smaller than the pore diameter of the protein-adsorbing porous membrane, and can pass through the pores. The molecular weight is preferably 1,000 to 1,000,000, more preferably 1,000 to 500,000, and still more preferably 1,000 to 300,000.

The washing step is carried out as required in order to increase the purification purity of the protein recovered in the elution step following the washing step. For example, the washing step is carried out in a case where when the adsorbed protein is recovered, it is desired to previously wash away turbid components contained in the stock solution adhering to the protein-adsorbing porous membrane and waste proteins to prevent them from being mixed into the protein recovered in the following elution step.

In this embodiment, in the elution step, the elution of the adsorbed protein by the passage of the eluent is performed. When the adsorbed protein is a desired protein, the permeating solution of the eluent that has permeated the protein-adsorbing porous membrane is recovered. In addition, when the adsorbed proteins are waste proteins, the permeating solution of the eluent that has permeated the protein-adsorbing porous membrane may be discarded.

In both cases, in this embodiment, in the elution step, one eluent may be passed, or a plurality of eluents may be switched and passed, and by passing at least one eluent in the opposite direction with respect to the direction of the passage of the stock solution in the adsorption step, the protein-adsorbing porous membrane is regenerated.

The method for purifying a protein in this embodiment may be a method for purifying a protein, using a protein-adsorbing porous membrane comprising a substrate and a polymer having protein adsorption ability coating the surface of the substrate, wherein when at least one eluent is passed through the protein-adsorbing porous membrane in an elution step after an adsorption step, at least any one of the above eluents is passed in the opposite direction with respect to the direction of the passage of a stock solution in the adsorption step.

In this embodiment, when elution is performed a plurality of times in the elution step, the eluent should be passed in the opposite direction with respect to the direction of the passage of the stock solution in the adsorption step at least once. The number of times the eluent is passed in the opposite direction is not particularly limited, and the eluent may be passed in the opposite direction a plurality of times. In all the plurality of times of elution, the eluent may be passed in the opposite direction with respect to the direction of the passage of the stock solution in the adsorption step.

In this embodiment, when the protein-adsorbing porous membrane is a flat membrane, and a liquid is passed from the front surface (one surface) to the back surface (the other surface) in the adsorption step, "a liquid is passed in the opposite direction" means that a liquid is passed from the back surface (the other surface) to the front surface (one surface). When the protein-adsorbing porous membrane is a hollow fiber membrane, and a liquid is passed from the inside (one surface) to the outside (the other surface) of the hollow fiber membrane in the adsorption step, "a liquid is passed in the opposite direction" means that a liquid is passed from the outside (the other surface) to the inside (one surface). When a liquid is passed from the outside (the other surface) to the inside (one surface) of the hollow fiber membrane in the adsorption step, "a liquid is passed in the opposite direction" means that a liquid is passed from the inside (one surface) to the outside (the other surface). In this embodiment, when a liquid is passed in the opposite direction using a module, this can be performed by changing the module inlet and outlet for liquid passage in the adsorption step and passing the liquid from the outlet side to the inlet side. The switching between the module inlet side and outlet side can also be performed by switching the valve in the piping of the apparatus to which the module is attached, and can also be performed by removing the module from the apparatus once and changing the direction of the attachment of the module.

The eluent used in the elution step in this embodiment is not particularly limited as long as the adsorbed protein can be eluted.

The eluent is selected from the group consisting of an aqueous solution comprising a salt, an aqueous solution whose pH is adjusted, water, an organic solvent, and a mixed solution thereof. One or more suitable ones can be selected according to each process, such as the type of the adsorbed protein, the separation purpose, and the type of the functional group having protein adsorption ability (a hydrophobic interaction membrane, an ion exchange membrane, a group-specific affinity adsorption membrane, or an individual-specific affinity adsorption membrane). At least one eluent passed in the opposite direction with respect to the direction of the passage of the stock solution in the adsorption step is selected from the above eluents.

Examples of the "mixed solution" include a mixed solution obtained by mixing an aqueous solution comprising a salt, an aqueous solution whose pH is adjusted, or water, and an organic solvent in the desired proportion.

Examples of the "organic solvent" include organic solvents usually used in the purification of a protein, for example, alcohol-based solvents, such as ethanol, and nitrile-based solvents, such as acetonitrile.

Examples of the "aqueous solution whose pH is adjusted" include an aqueous solution whose pH is adjusted with an alkali (for example, an aqueous solution of NaOH) or an acid (for example, hydrochloric acid) and also include a buffer adjusted to the desired pH. A buffer comprising a neutral salt, and the like, which will be described in detail later, are not classified into the "aqueous solution whose pH is adjusted." The buffer comprising a neutral salt is classified into the "aqueous solution comprising a salt" for convenience in this embodiment, but this is not to classify substantial differences in the effect of elution as the eluent.

When it is necessary to recover the adsorbed protein, an eluent adjusted at a stable pH for the adsorbed protein is preferably used. The stable pH means a pH region in which the adsorbed protein does not denature.

In a case where the "aqueous solution whose pH is adjusted" is used, whether the direction of liquid passage in the elution step is the forward direction or the opposite direction with respect to the direction of the passage of the stock solution in the adsorption step, a neutralization operation is preferably subsequently performed. The liquid passage in such a neutralization operation may also be in the forward direction or in the opposite direction. In the neutralization operation, a buffer comprising a salt adjusted to the desired pH may be used as the "aqueous solution comprising a salt," or a buffer adjusted to the desired pH can also be used as the "aqueous solution whose pH is adjusted."

The "salt" of the "aqueous solution comprising a salt" means a neutral salt, preferably a salt such as NaCl (sodium chloride) or KCl (potassium chloride).

A simple aqueous solution comprising a salt is neither acidic nor basic and is neutral, but the "aqueous solution comprising a salt" in this embodiment comprises a neutral salt and further may be a pH-adjusted buffer. In other words, a buffer comprising a neutral salt is classified into the "aqueous solution comprising a salt."

The adsorption of a protein is possible in a solution comprising a salt at low concentration as described in Patent Literature 1, and therefore, the salt concentration is preferably 0.3 mol/L or more, more preferably 0.5 mol/L or more, further preferably 0.8 mol/L or more, and still further preferably 1 mol/L or more in order to perform more efficient elution. An aqueous solution comprising a neutral salt at 0.3 mol/L or more and a concentration, or less, at which the mechanical strength and shape of the protein-adsorbing porous membrane are retained and there are no problems with liquid passage pressure and the like in use is preferably passed in this embodiment. Such liquid passage may be in the forward direction or in the opposite direction.

The salt concentration is the concentration of a neutral salt, and the concentration of other solutes does not matter. Therefore, from a simple aqueous solution of a neutral salt, a buffer comprising a neutral salt, and the like, an appropriate one can be selected.

A buffer is generally passed for the equilibration of a protein-adsorbing porous membrane in an elution step. Therefore, from the viewpoint of the simplification of operation considering going to the adsorption step again, a buffer comprising a salt adjusted to the same pH as the stock solution in the elution step is preferably used.

In a protein-adsorbing porous membrane of a group-specific affinity adsorption membrane or an individual-specific affinity adsorption membrane, the elution of the adsorbed protein by pH change is possible, and a suitable aqueous solution whose pH is adjusted is preferably used.

As has been described above, in this embodiment, the ion exchange membrane is a protein-adsorbing porous membrane in which the functional group having protein adsorption ability is an ion exchange functional group. The ion exchange membrane as the protein-adsorbing porous membrane is highly versatile and therefore can be preferably used in the solution of the problem by the purification method in this embodiment.

This embodiment in the ion exchange membrane will be more specifically described below.

In the ion exchange membrane, at least an eluent comprising an "aqueous solution comprising a salt" or an "aqueous solution whose pH is adjusted" can be selected as the eluent in the elution step.

Among ion exchange membranes, all of a strongly acidic cation exchange membrane, a weakly acidic cation exchange membrane, a strongly basic anion exchange membrane, and a weakly basic anion exchange membrane can use the "aqueous solution comprising a salt" as the eluent. Particularly, in the weakly acidic cation exchange membrane and the weakly basic anion exchange membrane, the "aqueous solution whose pH is adjusted" can also be used as the eluent.

Usually, the total charge of a protein in an aqueous solution is zero at a pH at the isoelectric point (pI), and the protein is negatively charged at a pH more than pI and positively charged at a pH less than pI. In addition, the weakly acidic cation exchange membrane and the weakly basic anion exchange membrane also depend on pH.

The weakly acidic cation exchange membrane has no charge deviation at the pI of the membrane or less and is negatively charged at more than the pI. Therefore, in a pH region at the pI of the protein or more and the pI of the membrane or more, both are negatively charged, and therefore, the adsorbed protein is eluted. In addition, also at the pI of the protein or less and the pI of the membrane or less, the electrostatic interaction between both disappears, and therefore, the adsorbed protein is eluted. In other words, the pH region in which the protein can be adsorbed on the membrane is between the pI of the protein and the pI of the membrane, and the "aqueous solution whose pH is adjusted" in a pH region other than this can be used as the eluent.

Also in the weakly basic anion exchange membrane, similarly, the weakly basic anion exchange membrane has no charge deviation at the pI of the membrane or more and is positively charged at less than the pI. Therefore, in a pH region at the pI of the protein or more and the pI of the membrane or more, the electrostatic interaction between both disappears, and therefore, the adsorbed protein is eluted. In addition, also at the pI of the protein or less and the pI of the membrane or less, both are positively charged, and therefore, the adsorbed protein is eluted. In other words, the pH region in which the protein can be adsorbed on the membrane is between the pI of the protein and the pI of the membrane, and the "aqueous solution whose pH is adjusted" in a pH region other than this can be used as the eluent. Here, the pI of the membrane can be obtained by a streaming potential method.

From the above, in this embodiment, when the protein-adsorbing porous membrane is the weakly basic anion exchange membrane or the weakly acidic cation exchange membrane, the "aqueous solution whose pH is adjusted" can be used as an eluent having a pH at other than between the isoelectric point of the adsorbed protein and the isoelectric point of the above protein-adsorbing porous membrane. However, for efficient elution, an eluent having a pH further away from the pH threshold is preferably used. Specifically, the pH threshold ±1 is preferred, the pH threshold ±2 is more preferred, and the pH threshold ±3 or more is further preferred. In addition, as the solute for adjusting pH, NaOH or HCl is preferably used. Here, the pH threshold means a pH at either of the pI of the protein or the pI of the membrane.

In a case where the weakly basic anion exchange membrane or the weakly acidic cation exchange membrane is used as the protein-adsorbing porous membrane, when the "aqueous solution whose pH is adjusted" is used (step (B)) in the elution step, the "aqueous solution comprising a salt," preferably a buffer comprising a salt, is preferably subsequently passed (step (C)). By the step (B) and the step (C), the charge state of the membrane can be returned to the equilibration state for protein adsorption with a small amount of liquid passage.

In this embodiment, more preferably, after the step of passing the "aqueous solution comprising a salt" (A), the step of passing the "aqueous solution whose pH is adjusted" (B) is performed, and then, the step of passing the "aqueous solution comprising a salt" (C) is performed again.

Elution may be performed by suddenly changing pH in the protein adsorption state. But, by performing the step (A) and performing the step (B) from the viewpoint of preventing the denaturation of the adsorbed protein due to pH change, the efficiency of the elution of the adsorbed protein can be increased.

In this embodiment, preferably, the liquid is passed in the opposite direction with respect to the direction of the passage of the stock solution in the adsorption step in any of the step (A), the step (B), and the step (C). More preferably, the liquid is passed in the opposite direction in any of the step (B) and the step (C), and further preferably, both eluents in the step (B) and the step (C) are passed in the opposite direction with respect to the direction of the passage of the stock solution in the adsorption step for good elution efficiency.

The liquid passage rate at which the eluent is passed through the protein-adsorbing porous membrane in the elution step can be arbitrarily set in the range of a rate, or more, at which the adsorbed protein is eluted and a rate, or less, at which the shape of the protein-adsorbing porous membrane and its module is maintained and the adsorption function can be maintained.

In the case of a module-molded, hollow fiber-shaped, protein-adsorbing porous membrane, when the liquid is passed in the internal pressure mode (liquid passage from the inside to the outside), 1 MV/min to 110 MV/min is preferred, 3 MV/min to 40 MV/min is more preferred, and 4 MV/min to 15 MV/min is further preferred. When the liquid is passed in the external pressure mode (liquid passage from the outside to the inside), 1 MV/min to 15 MV/min is preferred, 3 MV/min to 10 MV/min is more preferred, and 4 MV/min to 10 MV/min is further preferred. Here, MV means membrane volume. In other words, 1 MV/min means that the same amount of the liquid as the membrane volume is passed for 1 minute. The method for calculating the membrane volume will be described in detail later.

The amount of liquid passage in which the eluent is passed through the protein-adsorbing porous membrane in the elution step can be arbitrarily set as long as it is an amount in which the adsorbed protein is sufficiently eluted. When a plurality of eluents are switched and passed, it is necessary to also consider the amount required for replacement. In the case of a module-molded, hollow fiber-shaped, protein-adsorbing porous membrane, 10 MV or more is preferred, 25 MV or more is more preferred, and 30 MV or more is further preferred for each eluent.

EXAMPLES

The present invention will be specifically described below by giving Examples and Comparative Examples. However, the present invention is not limited to these Examples.

Manufacturing Example 1

Manufacturing of Hollow Fiber Porous Membrane as Polymer Substrate 27.2 parts by mass of fine powder silicic acid (AEROSIL (registered trademark) R972 grade), 54.3 parts by mass of dibutyl phthalate (DBP), and 18.5 parts by mass of a polyethylene resin powder (SUNFINE (trademark) SH-800 grade manufactured by Asahi Kasei Chemicals Corporation) were premixed and extruded into a hollow fiber shape by a twin screw extruder to obtain a hollow fiber-shaped membrane. Then, this membrane was sequentially immersed in methylene chloride and an aqueous solution of sodium hydroxide to extract the dibutyl phthalate (DBP) and the silicic acid followed by water washing and drying treatment to obtain a hollow fiber porous membrane made of polyethylene.

The average pore diameter of the obtained hollow fiber porous membrane measured by the bubble point method was 0.3 μm. The measurement was performed according to the method for measuring average pore diameter (another name: half dry method) described in ASTM standard F316-86. The measurement was performed on the hollow fiber porous membrane 6 cm long using ethanol as a liquid and nitrogen as a pressurization gas. For the obtained half dry average pressure, the average pore diameter was calculated by the following formula (6).

The porosity was 69%. The porosity was calculated by the following formula (7).

[Expression 6]

$$\text{average pore diameter}[\mu m] = \frac{2860 \times \gamma}{p} \quad (6)$$

γ: surface tension (dynes/cm)
p: half dry average pressure (Pa)

[Expression 7]

$$\text{porosity}[\%] = \frac{(W_{wet} - W_{dry})/\rho}{V} \quad (7)$$

$W_{wet}$: weight of hollow fiber porous membrane during water wetting (g)
$W_{dry}$: weight of hollow fiber porous membrane during drying (g)
ρ: density of water at water temperature during measurement (g/mL)
V: annular cross-sectional area volume of hollow fiber (mL)

In the case of a flat membrane, V represents membrane volume, and the membrane volume is obtained as a value obtained by multiplying membrane area by membrane thickness. Here, the annular cross-sectional area volume of the hollow fiber (V) was calculated by the following formula (8).

[Expression 8]

$$V = L\left\{\left(\frac{D_o}{2}\right)^2 - \left(\frac{D_i}{2}\right)^2\right\} \times \pi \quad (8)$$

L: length of hollow fiber used for measurement (cm)
$D_o$: outer diameter of hollow fiber (cm)
$D_i$: inner diameter of hollow fiber (cm)

Manufacturing Example 2

Manufacturing of Hollow Fiber Porous Membrane Having Adsorption Ability

The hollow fiber porous membrane made of polyethylene manufactured in Manufacturing Example 1 was placed in a sealed container, and nitrogen replacement was performed in the container. Then, the sealed container in which the hollow fiber porous membrane was placed was placed in a box made of expanded polystyrene together with dry ice, and irradiated with 200 kGy of γ rays while being cooled, to allow the polyethylene to generate radicals to activate the hollow fiber porous membrane.

The activated hollow fiber porous membrane was returned to room temperature in the sealed container having a nitrogen atmosphere. Then, the hollow fiber porous membrane was introduced into a reaction container, and the reaction container was sealed and brought into a vacuum state (100 Pa or less). A reaction liquid previously prepared by mixing 5 parts by mass of glycidyl methacrylate (GMA) and 95 parts by mass of methanol and performing nitrogen bubbling was fed into the reaction container in the vacuum state utilizing pressure difference. The fed reaction liquid was circulated at 40° C. for 4 hours and allowed to stand overnight, and then, the reaction liquid was discharged. The hollow fiber porous membrane was sufficiently washed with methanol and then water to obtain a grafted hollow fiber porous membrane in which glycidyl methacrylate was graft-polymerized onto a polyethylene main chain.

Part of the obtained grafted hollow fiber membrane was taken and dried, and the weight was measured. The degree of grafting was calculated by formula (1). The degree of grafting was 66 to 73%.

An aqueous solution of diethylamine at a volume concentration of 50 was placed in a reaction container in which the grafted hollow fiber porous membrane was placed, circulated at 30° C. for 5 hours, and allowed to stand overnight, and then, the aqueous solution of diethylamine was discharged. Then, the hollow fiber porous membrane was sufficiently washed with water and dried to obtain a grafted hollow fiber porous membrane having a diethylamino group in a graft chain as a protein-adsorbing porous membrane.

Part of the obtained protein-adsorbing porous membrane was taken and dried, and the weight was measured. The ligand conversion rate was calculated by formula (2). The ligand conversion rate was 91%.

In addition, the outer diameter and inner diameter of the protein-adsorbing porous membrane were 3.6 mm and 2.2 mm, respectively.

Manufacturing Example 3

Module Molding

The protein-adsorbing porous membrane manufactured in Manufacturing Example 2 was molded into a module with a fiber effective length of 9.4 cm and one fiber contained.
[Evaluation of Adsorption Ability of Protein-Adsorbing Porous Membrane]

As terms representing the adsorption ability of a protein-adsorbing porous membrane, there are "equilibrium adsorption capacity" (or "static adsorption capacity") and "dynamic adsorption capacity," which are widely used in the industry.

The "dynamic adsorption capacity" refers to adsorption capacity until a point at which, when a stock solution comprising a protein is passed through a protein-adsorbing porous membrane, the protein concentration in the permeating solution of the stock solution reaches reference concentration. This reference concentration is referred to as a breakthrough point. Generally, the breakthrough point is selected from a range in which the protein concentration in the permeating solution of a stock solution with respect to the protein concentration in the stock solution to be passed is in the range of 5% to 20%.

Generally, for the amount of adsorption, units suitable for representing its properties, such as weight, volume, and the number of moles, can be used. In addition, also for adsorption capacity represented as a unit amount of a protein-adsorbing porous membrane, not only unit volume, but units suitable for representing its properties, such as unit weight, can be used.

In obtaining adsorption capacity, the membrane volume is volume obtained by substituting effective membrane length contributing to adsorption for L in the above formula (8) in annular cross section volume (V) calculated by the formula. The effective membrane length is calculated by subtracting the length of a contact portion, such as a connector for connecting to an apparatus, (length not contributing to adsorption) from the length of a hollow fiber used for measurement. The membrane volume in the case of a flat membrane is a value obtained by multiplying effective membrane area by membrane thickness.

For the module manufactured according to Manufacturing Example 3, the measurement of equilibrium adsorption capacity and dynamic adsorption capacity was performed by connecting to a general-purpose HPLC system (AKTAexplorer 100, GE Healthcare Japan). From the same batches of protein-adsorbing porous membranes manufactured in Manufacturing Examples 1 and 2, a plurality of modules were made according to Manufacturing Example 3, and for the measurement of equilibrium adsorption capacity and the measurement of dynamic adsorption capacity, different module units were used. Both the equilibrium adsorption capacity and the dynamic adsorption capacity were obtained by monitoring the absorbance of the passed solution of a stock solution and subjecting the obtained chromatogram to numerical analysis. The dynamic adsorption capacity was calculated using as a breakthrough point the amount of the passed solution of a stock solution reaching 10% of the absorbance of a protein stock solution (1 mg/mL).

Evaluation Example 1

Degree of Multilayering

The specific surface area $S_M$ of the protein-adsorbing porous membrane obtained in Manufacturing Example 2 was 6.8 $m^2/g$. The measurement was performed by the BET method using a specific surface area and pore distribution measuring apparatus (COULTER SA3100 series) manufactured by BECKMAN COULTER.

Area occupied by one BSA molecule $S_P=16\times10^{-18}$ ($m^2$), molecular weight $M_r=67500$ (g/mol), and Avogadro's number $N_A=6.02\times10^{23}$ (/mol) were substituted into formula (5) for calculation to calculate a theoretical single-layer adsorption capacity of $4.8\times10^{-2}$ (g/g).

The equilibrium adsorption capacity was performed using BSA, and the 280 nm absorbance of the passed solution of a stock solution was monitored. The amount of equilibrium adsorption of BSA (the numerator of formula 4) was 45 mg, and the weight of the module-molded protein-adsorbing porous membrane W was 226 mg. Therefore, according to formula (4), the equilibrium adsorption capacity was 0.20 g/g.

Therefore, the degree of multilayering was calculated as 4.2 by formula (3).

Evaluation Example 2

Evaluation of Repeated Dynamic Adsorption Capacity

The module was connected to the above-described general-purpose HPLC system, and an adsorption step, a washing step, and an elution step were repeatedly performed. The dynamic adsorption capacity in the adsorption step was calculated. For the measurement, BSA was used, and the 280 nm absorbance of the passed solution of the stock solution was monitored.

The procedure of, after the adsorption step, undergoing the washing step and the elution step and measuring adsorption capacity was repeated a plurality of times, and dynamic adsorption capacity was measured each time. By taking the first dynamic adsorption capacity (that is, dynamic adsorption capacity when the protein was first adsorbed) as 100, the ratio of dynamic adsorption capacity during adsorption after the elution step was calculated as a "retention rate (%)," and the degree of the effect of the elution method was compared. It can be said that as the retention rate becomes closer to 100, the elution effect becomes larger.

For dynamic adsorption capacity, the amount of dynamic adsorption (mg) was divided by membrane volume V (mL) obtained by formula (8), and the unit was mg/mL.

In these Examples, the following reagents and the like were used.

<Tris Hydrochloride Buffer Solution (Buffer Solution)>

4.84 g of tris(hydroxymethyl)aminomethane (manufactured by NACALAI TESQUE, INC.) was dissolved in about 1.9 L of ultrapure water, and hydrochloric acid was added to adjust the solution to pH 8. Then, the solution was diluted in a measuring flask to 2 L at a concentration of 20 mmol/L (pH 8). Then, the solution was passed through a filter having a pore diameter of 0.45 μm and used.

<BSA Solution>

BSA (bovine serum albumin, manufactured by Sigma-Aldrich) generally used as a model protein was used. When the performance of a biotechnological purification apparatus is indicated, a purified protein solution is generally used as a model.

1 g of BSA was dissolved in 1 L of a 20 mmol/L (pH 8) tris hydrochloric acid buffer. The solution was passed through a filter having a pore diameter of 0.45 μm and used.

<Salt Buffer Solution>

4.84 g of tris(hydroxymethyl)aminomethane (manufactured by NACALAI TESQUE, INC.) was dissolved in about 1.9 L of ultrapure water, and then, 117 g of NaCl (special grade reagent manufactured by Wako Pure Chemical Industries, Ltd.) was dissolved, and then, hydrochloric acid was added to adjust the solution to pH 8. The solution was diluted in a measuring flask to 2 L to prepare a buffer comprising sodium chloride at a concentration of 1 mol/L. Then, the solution was passed through a filter having a pore diameter of 0.45 μm and used.

<Aqueous Solution of Sodium Hydroxide (Alkali)>

A 1 mol/L aqueous solution of sodium hydroxide (special grade reagent manufactured by Wako Pure Chemical Industries, Ltd.) was used.

The direction of the flow of the eluent in the elution step is described as the "forward direction" when the eluent is passed in the same direction as the direction of flow in the adsorption step, and described as the "opposite direction" when the eluent is passed in the opposite direction with respect to the direction of flow in the adsorption step. In addition, the evaluation flow rate was 5 MV/min in all steps in all Examples and Comparative Examples.

Example 1

For the module of the protein-adsorbing porous membrane obtained in Manufacturing Examples 1 to 3, an adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (15 mL, the forward direction), the aqueous solution of sodium hydroxide (20 mL, the opposite direction), and the salt buffer (20 mL, the opposite direction) were passed.

The dynamic adsorption capacity in the first adsorption was 47.7 mg/mL, and the dynamic adsorption capacity after 10 times of repetition was 45.9 mg/mL, and the retention rate was 96%.

Example 2

For the module of the protein-adsorbing membrane porous membrane obtained in Manufacturing Examples 1 to 3, an adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (15 mL, the forward direction), the aqueous solution of sodium hydroxide (20 mL, the forward direction), and the salt buffer (20 mL, the opposite direction) were passed.

The dynamic adsorption capacity in the first adsorption was 58.6 mg/mL, and the dynamic adsorption capacity after 10 times of repetition was 50.5 mg/mL, and the retention rate was 86%.

Example 3

For the module of the protein-adsorbing membrane porous membrane obtained in Manufacturing Examples 1 to 3, an adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (15 mL, the forward direction), the aqueous solution of sodium hydroxide (20 mL, the opposite direction), and the salt buffer (20 mL, the forward direction) were passed.

The dynamic adsorption capacity in the first adsorption was 51.4 mg/mL, and the dynamic adsorption capacity after 10 times of repetition was 43.5 mg/mL, and the retention rate was 85%.

Comparative Example 1

For the module of the protein-adsorbing membrane porous membrane obtained in Manufacturing Examples 1 to 3, liquid passage was performed with the same eluents, order of liquid passage, and amount of liquid passage as Example 1 except that in the elution step, all were passed in the forward direction.

An adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (15 mL, the forward direction), the aqueous solution of sodium hydroxide (20 mL, the forward direction), and the salt buffer (20 mL, the forward direction) were passed.

The dynamic adsorption capacity in the first adsorption was 51.2 mg/mL, and the dynamic adsorption capacity after 10 times of repetition was 40.0 mg/mL, and the retention rate was 78%.

Comparative Example 2

For the module of the protein-adsorbing membrane porous membrane obtained in Manufacturing Examples 1 to 3, an adsorption step (30 mL of the buffer, 40 mL of the BSA solution) was performed in an internal pressure mode (liquid passage from the inside to the outside of the hollow portion), and then, as a washing step, 10 mL of the buffer was passed in the opposite direction, and then, 10 mL of the buffer was passed in the forward direction. Then, as an elution step, the salt buffer (15 mL, the forward direction), the aqueous solution of sodium hydroxide (20 mL, the forward direction), and the salt buffer (20 mL, the forward direction) were passed.

The dynamic adsorption capacity in the first adsorption was 55.5 mg/mL, and the dynamic adsorption capacity after 10 times of repetition was 42.7 mg/mL, and the retention rate was 77%.

The results of Examples 1 to 3 and Comparative Examples 1 and 2 are shown in Table 1.

Example 4

An Example in which an elution step is performed using the salt buffer as one type of eluent is shown.

For the module of the protein-adsorbing membrane porous membrane obtained in Manufacturing Examples 1 to 3, an adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (20 mL, the opposite direction) was passed.

TABLE 1

| Step | Order of liquid passage | Type of passed liquid | Example 1 Amount of liquid passage (Direction) | Example 2 Amount of liquid passage (Direction) | Example 3 Amount of liquid passage (Direction) | Comparative Example 1 Amount of liquid passage (Direction) | Comparative Example 2 Amount of liquid passage (Direction) |
|---|---|---|---|---|---|---|---|
| Treatment conditions | | | | | | | |
| Adsorption step | 1 | Buffer | 30 mL (Forward) | 30 mL (Forward) | 30 mL (Forward) | 30 mL (Forward) | 30 mL (Forward) |
| | 2 | BSA solution | 40 mL (Forward) | 40 mL (Forward) | 40 mL (Forward) | 40 mL (Forward) | 40 mL (Forward) |
| Washing step | 3 | Buffer | 10 mL (Forward) | 10 mL (Forward) | 10 mL (Forward) | 10 mL (Forward) | 10 mL (Opposite) 10 mL (Forward) |
| Elution step | 4 | Salt buffer | 15 mL (Forward) | 15 mL (Forward) | 15 mL (Forward) | 15 mL (Forward) | 15 mL (Forward) |
| | 5 | Alkali | 20 mL (Opposite) | 20 mL (Forward) | 20 mL (Opposite) | 20 mL (Forward) | 20 mL (Forward) |
| | 6 | Salt buffer | 20 mL (Opposite) | 20 mL (Opposite) | 20 mL (Forward) | 20 mL (Forward) | 20 mL (Forward) |
| Results | | | | | | | |
| | | | (Adsorption capacity unit: mg/mL) | | | | |
| Number of times of repetition/times | | | Adsorption capacity (Retention rate) | Adsorption capacity (Retention rate) | Adsorption capacity (Retention rate) | Adsorption capacity (Retention rate) | Adsorption capacity (Retention rate) |
| 1 | | | 47.7 (100%) | 58.6 (100%) | 51.4 (100%) | 51.2 (100%) | 55.5 (100%) |
| 2 | | | 47.7 (100%) | 58.6 (100%) | 51.2 (100%) | 50.9 (99%) | 54.4 (98%) |
| 3 | | | 47.5 (100%) | 57.9 (99%) | 50.4 (98%) | 49.9 (97%) | 53.3 (96%) |
| 4 | | | 47.5 (100%) | 57 (97%) | 49.5 (96%) | 49 (96%) | 52.2 (94%) |
| 5 | | | 47.5 (100%) | 56.7 (97%) | 48.9 (95%) | 47.7 (93%) | 51.6 (93%) |
| 6 | | | 47.4 (99%) | 55.7 (95%) | 47.5 (93%) | 46.2 (90%) | 50.0 (90%) |
| 7 | | | 47.4 (99%) | 54.4 (93%) | 46.7 (91%) | 44.9 (88%) | 0.5 (87%) |
| 8 | | | 47.4 (99%) | 53.5 (91%) | 45.7 (89%) | 43.2 (84%) | 46.1 (83%) |
| 9 | | | 47 (99%) | 52.2 (89%) | 44.7 (87%) | 41.9 (82%) | 44.4 (80%) |
| 10 | | | 45.9 (96%) | 50.5 (86%) | 43.5 (85%) | 40 (78%) | 42.7 (77%) |

In Comparative Example 1, the retention rate was 78%, whereas the retention rate was 96% in Example 1, 86% in Example 2, and 85% in Example 3. The effect of passing the eluent in the opposite direction with respect to the direction of adsorption was demonstrated.

In Comparative Example 2, when the buffer was passed in the opposite direction in the washing step, the adsorption capacity retention rate was 77% after 10 times of repetition. The effect of passing the eluent in the opposite direction in Examples 1 to 3 was demonstrated.

The dynamic adsorption capacity in the first adsorption was 49.5 mg/mL, and the dynamic adsorption capacity after 10 times of repetition was 42.2 mg/mL, and the retention rate was 85%.

Comparative Example 3

For the module of the protein-adsorbing membrane porous membrane obtained in Manufacturing Examples 1 to 3, liquid passage was performed with the same eluents and amount of liquid passage as Example 4 except that in the elution step, all were passed in the forward direction.

An adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (20 mL, the forward direction) was passed.

The dynamic adsorption capacity in the first adsorption was 38.7 mg/mL, and the dynamic adsorption capacity after 10 times of repetition was 27.5 mg/mL, and the retention rate was 71%.

The results of Example 4 and Comparative Example 3 are shown in Table 2.

TABLE 2

| | | | Example 4 | Comparative Example 3 |
|---|---|---|---|---|
| Treatment conditions | | | | |
| Step | Order of liquid passage | Type of passed liquid | Amount of liquid passage (Direction) | Amount of liquid passage (Direction) |
| Adsorption step | 1 | Buffer | 30 mL (Forward) | 30 mL (Forward) |
| | 2 | BSA solution | 40 mL (Forward) | 40 mL (Forward) |
| Washing step | 3 | Buffer | 10 mL (Forward) | 10 mL (Forward) |
| Elution step | 4 | Salt buffer | 20 mL (Opposite) | 20 mL (Forward) |
| Results | | | | |
| | | | (Adsorption capacity unit: mg/mL) | |
| Number of times of repetition/times | | | Adsorption capacity (Retention rate) | Adsorption capacity (Retention rate) |
| 1 | | | 49.5 (100%) | 38.7 (100%) |
| 2 | | | 49.4 (100%) | 37.5 (97%) |
| 3 | | | 48.7 (98%) | 36.4 (94%) |
| 4 | | | 48 (97%) | 35.2 (91%) |
| 5 | | | 47 (95%) | 34 (88%) |
| 6 | | | 46.2 (93%) | 32.9 (85%) |
| 7 | | | 45.2 (91%) | 31.5 (81%) |
| 8 | | | 44 (89%) | 30 (78%) |
| 9 | | | 43.2 (87%) | 28.9 (75%) |
| 10 | | | 42.2 (85%) | 27.5 (71%) |

In Comparative Example 3, the retention rate was 71%, whereas in Example 4, the retention rate was 85%. The effect of passing the eluent in the opposite direction with respect to the direction of adsorption was demonstrated.

The results of cases where an eluent was passed through protein-adsorbing porous membranes having various degrees of grafting and degrees of multilayering in the opposite direction in Examples 5 to 11 and Comparative Examples 4 to 10 are shown below (The results are shown together in Table 3).

TABLE 3

| | Example 5 | Comparative Example 4 | Example 6 | Comparative Example 5 | Example 7 | Comparative Example 6 | Example 8 | Comparative Example 7 |
|---|---|---|---|---|---|---|---|---|
| Type of membrane | | | | | | | | |
| membrane shape | Hollow fiber membrane | | Hollow fiber membrane | | Hollow fiber membrane | | Hollow fiber membrane | |
| Degree of grafting [%] | 195 | | 131 | | 85 | | 50 | |
| Ligand conversion rate [%] | 98 | | 97 | | 95 | | 98 | |
| Degree of multilayering | 5.5 | | 4.5 | | 4.3 | | 3.8 | |
| Details of treatment | | | | | | | | |
| Elution in opposite direction | Performed | Not performed | Performed | Not performed | Performed | Not performed | Performed | Not performed |
| Results | | | | | | | | |
| Number of times of repetition/times | Upper row: Dynamic adsorption capacity [mg/mL] Lower row: Retention rate [%] | | | | | | | |
| 1 | 73.9 | 75.0 | 56.4 | 56.0 | 55.0 | 54.4 | 46.0 | 46.4 |
| | 100 | 100 | 100 | 100 | 100 | 100 | 100 | 100 |
| 2 | 73.8 | 71.3 | 56.1 | 53.8 | 54.9 | 52.8 | 45.8 | 45.5 |
| | 100 | 95 | 99 | 96 | 100 | 97 | 100 | 98 |

TABLE 3-continued

| | | | | | | | | |
|---|---|---|---|---|---|---|---|---|
| 3 | 73.5 | 68.3 | 55.8 | 52.1 | 54.8 | 51.7 | 45.7 | 44.1 |
| | 99 | 91 | 99 | 93 | 100 | 95 | 99 | 95 |
| 4 | 72.6 | 65.3 | 55.4 | 50.4 | 54.8 | 50.0 | 45.6 | 43.2 |
| | 98 | 87 | 98 | 90 | 100 | 92 | 99 | 93 |
| 5 | 72.3 | 63.0 | 55.2 | 48.2 | 54.7 | 48.4 | 45.5 | 41.8 |
| | 98 | 84 | 98 | 86 | 99 | 89 | 99 | 90 |
| 6 | 71.4 | 60.0 | 55.0 | 46.5 | 54.5 | 46.8 | 45.3 | 40.4 |
| | 97 | 80 | 98 | 83 | 99 | 86 | 98 | 87 |
| 7 | 70.9 | 57.8 | 54.5 | 44.2 | 54.3 | 45.7 | 45.2 | 39.0 |
| | 96 | 77 | 97 | 79 | 99 | 84 | 98 | 84 |
| 8 | 70.5 | 56.3 | 54.2 | 42.6 | 54.1 | 44.1 | 44.8 | 38.1 |
| | 95 | 75 | 96 | 76 | 98 | 81 | 97 | 82 |
| 9 | 70.2 | 54.8 | 54.1 | 41.4 | 54.1 | 42.4 | 44.7 | 36.7 |
| | 95 | 73 | 96 | 74 | 98 | 78 | 97 | 79 |
| 10 | 69.5 | 52.7 | 54.1 | 40.9 | 53.9 | 41.0 | 44.6 | 35.9 |
| | 94 | 70 | 96 | 73 | 98 | 75 | 97 | 77 |
| Degree of improvement in retention rate | 134 | — | 131 | — | 130 | — | 125 | — |

| | Example 9 | Comparative Example 8 | Example 10 | Comparative Example 9 | Example 11 | Comparative Example 10 |
|---|---|---|---|---|---|---|
| | | | Type of membrane | | | |
| membrane shape | Hollow fiber membrane | | Hollow fiber membrane | | Flat membrane | |
| Degree of grafting [%] | 32 | | 14 | | 8 | |
| Ligand conversion rate [%] | 96 | | 97 | | 96 | |
| Degree of multilayering | 2.3 | | 1.6 | | 1.2 | |
| | | | Details of treatment | | | |
| Elution in opposite direction | Performed | Not performed | Performed | Not performed | Performed | Not performed |
| | | | Results | | | |
| Number of times of repetition/times | Upper row: Dynamic adsorption capacity [mg/mL] Lower row: Retention rate [%] | | | | | |
| 1 | 21.1 | 21.4 | 10.4 | 10.6 | 7.7 | 8.4 |
| | 100 | 100 | 100 | 100 | 100 | 100 |
| 2 | 21.1 | 20.9 | 10.4 | 10.6 | 7.7 | 8.3 |
| | 100 | 98 | 100 | 100 | 99 | 99 |
| 3 | 21.0 | 20.7 | 10.3 | 10.5 | 7.6 | 8.3 |
| | 100 | 97 | 99 | 99 | 99 | 99 |
| 4 | 21.0 | 20.3 | 10.3 | 10.4 | 7.6 | 8.3 |
| | 99 | 95 | 99 | 98 | 99 | 98 |
| 5 | 20.9 | 20.1 | 10.2 | 10.3 | 7.5 | 8.2 |
| | 99 | 94 | 98 | 97 | 98 | 98 |
| 6 | 20.8 | 19.7 | 10.2 | 10.2 | 7.5 | 8.1 |
| | 99 | 92 | 98 | 96 | 98 | 97 |
| 7 | 20.8 | 19.4 | 10.2 | 10.1 | 7.5 | 8.1 |
| | 99 | 91 | 98 | 95 | 98 | 96 |
| 8 | 20.8 | 19.0 | 10.1 | 10.1 | 7.5 | 8.0 |
| | 98 | 89 | 97 | 95 | 98 | 96 |
| 9 | 20.7 | 18.8 | 10.1 | 10.0 | 7.5 | 8.0 |
| | 98 | 88 | 97 | 94 | 97 | 95 |
| 10 | 20.7 | 18.5 | 10.1 | 9.9 | 7.5 | 7.9 |
| | 98 | 87 | 97 | 93 | 97 | 94 |
| Degree of improvement in retention rate | 113 | — | 104 | — | 103 | — |

Example 5

The protein-adsorbing porous membrane was obtained by a graft reaction using the hollow fiber porous membrane made of polyethylene manufactured in Manufacturing Example 1 as a substrate. The graft reaction followed Manufacturing Example 2 except that the mixing ratio of glycidyl methacrylate (GMA):methanol in the reaction liquid was 13.9 parts by mass:86.1 parts by mass. The degree of grafting and ligand conversion rate of the obtained protein-adsorbing porous membrane was 195% and 98%, respectively. In addition, the outer diameter was 4.4 mm, and the inner diameter was 2.8 mm.

Three of the obtained protein-adsorbing porous membranes were taken, and modules (5A, 5B, and 5C) were molded as in Manufacturing Example 3.

For the module 5A, according to Evaluation Example 1, measurement was carried out and the degree of multilayering was calculated. The degree of multilayering was 5.5.

For the module 5B, the evaluation of repeated dynamic adsorption capacity was carried out according to Evaluation Example 2. An adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (15 mL, the forward direction), the aqueous solution of sodium hydroxide (20 mL, the opposite direction), and the salt buffer (20 mL, the opposite direction) were passed.

The dynamic adsorption capacity in the first adsorption was 73.9 mg/mL, and the dynamic adsorption capacity after 10 times of repetition was 69.5 mg/mL, and the retention rate was 94%.

Comparative Example 4

Evaluation was performed as in Example 5 except that for the module 5C manufactured in Example 5, all eluents were passed in the forward direction, the salt buffer (15 mL, the forward direction), the aqueous solution of sodium hydroxide (20 mL, the forward direction), and the salt buffer (20 mL, the forward direction), in the elution step.

The dynamic adsorption capacity in the first adsorption was 75.0 mg/mL, and the amount of dynamic adsorption capacity after 10 times of repetition was 52.7 mg/mL, and the retention rate was 70%.

In the case of a degree of multilayering of 5.5, the retention rate in Comparative Example 4 was 70%, whereas in Example 5, the retention rate was 94% and the retention rate was improved. The degree of improvement in retention rate was 134% when represented by (the retention rate when elution was carried out in the opposite direction)/(the retention rate when elution was carried out only in the forward direction).

Example 6

The protein-adsorbing porous membrane was obtained by a graft reaction using the hollow fiber porous membrane made of polyethylene manufactured in Manufacturing Example 1 as a substrate. The graft reaction followed Manufacturing Example 2 except that the mixing ratio of glycidyl methacrylate (GMA):methanol in the reaction liquid was 9.4 parts by mass:90.6 parts by mass. The degree of grafting and ligand conversion rate of the obtained protein-adsorbing porous membrane was 131% and 97%, respectively. In addition, the outer diameter was 4.1 mm, and the inner diameter was 2.5 mm.

Three of the obtained protein-adsorbing porous membranes were taken, and modules (6A, 6B, and 6C) were molded as in Manufacturing Example 3.

For the module 6A, according to Evaluation Example 1, measurement was carried out and the degree of multilayering was calculated. The degree of multilayering was 4.5.

For the module 6B, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Example 5. (In other words, in the elution step, liquid passage in the opposite direction was performed.)

The dynamic adsorption capacity in the first adsorption was 56.4 mg/mL, and the dynamic adsorption capacity after 10 times of repetition was 54.1 mg/mL, and the retention rate was 96%.

Comparative Example 5

For the module 6C manufactured in Example 6, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Comparative Example 4. (In other words, in the elution step, all eluents were passed in the forward direction.)

The dynamic adsorption capacity in the first adsorption was 56.0 mg/mL, and the amount of dynamic adsorption after 10 times of repetition was 40.9 mg/mL, and the retention rate was 73%.

In the case of a degree of multilayering of 4.5, the retention rate in Comparative Example 5 was 73%, whereas in Example 6, the retention rate was 96% and the retention rate was improved. The degree of improvement in retention rate was 131%.

Example 7

The protein-adsorbing porous membrane was obtained by a graft reaction using the hollow fiber porous membrane made of polyethylene manufactured in Manufacturing Example 1 as a substrate. The graft reaction followed Manufacturing Example 2 except that the mixing ratio of glycidyl methacrylate (GMA):methanol in the reaction liquid was 6.1 parts by mass:93.9 parts by mass. The degree of grafting and ligand conversion rate of the obtained protein-adsorbing porous membrane was 85% and 95%, respectively. In addition, the outer diameter was 3.8 mm, and the inner diameter was 2.4 mm.

Three of the obtained protein-adsorbing porous membranes were taken, and modules (7A, 7B, and 7C) were molded as in Manufacturing Example 3.

For the module 7A, according to Evaluation Example 1, measurement was carried out and the degree of multilayering was calculated. The degree of multilayering was 4.3.

For the module 7B, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Example 5. (In other words, in the elution step, liquid passage in the opposite direction was performed.)

The dynamic adsorption capacity in the first adsorption was 55.0 mg/mL, and the dynamic adsorption capacity after 10 times of repetition was 53.9 mg/mL, and the retention rate was 98%.

Comparative Example 6

For the module 7C manufactured in Example 7, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Comparative Example 4. (In other words, in the elution step, all eluents were passed in the forward direction.)

The dynamic adsorption capacity in the first adsorption was 54.4 mg/mL, and the amount of dynamic adsorption after 10 times of repetition was 41.0 mg/mL, and the retention rate was 75%.

In the case of a degree of multilayering of 4.3, the retention rate in Comparative Example 6 was 75%, whereas in Example 7, the retention rate was 98% and the retention rate was improved. The degree of improvement in retention rate was 130%.

Example 8

The protein-adsorbing porous membrane was obtained by a graft reaction using the hollow fiber porous membrane made of polyethylene manufactured in Manufacturing Example 1 as a substrate. The graft reaction followed Manufacturing Example 2 except that the mixing ratio of glycidyl methacrylate (GMA):methanol in the reaction liquid was 3.6 parts by mass:96.4 parts by mass. The degree of grafting and ligand conversion rate of the obtained protein-adsorbing porous membrane was 50% and 98%, respectively. In addition, the outer diameter was 3.4 mm, and the inner diameter was 2.1 mm.

Three of the obtained protein-adsorbing porous membranes were taken, and modules (8A, 8B, and 8C) were molded as in Manufacturing Example 3.

For the module 8A, according to Evaluation Example 1, measurement was carried out and the degree of multilayering was calculated. The degree of multilayering was 3.8.

For the module 8B, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Example 5. (In other words, in the elution step, liquid passage in the opposite direction was performed.)

The dynamic adsorption capacity in the first adsorption was 46.0 mg/mL, and the dynamic adsorption capacity after 10 times of repetition was 44.6 mg/mL, and the retention rate was 97%.

Comparative Example 7

For the module 8C manufactured in Example 8, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Comparative Example 4. (In other words, in the elution step, all eluents were passed in the forward direction.)

The dynamic adsorption capacity in the first adsorption was 46.4 mg/mL, and the amount of dynamic adsorption after 10 times of repetition was 35.9 mg/mL, and the retention rate was 77%.

In the case of a degree of multilayering of 3.8, the retention rate in Comparative Example 7 was 77%, whereas in Example 8, the retention rate was 97% and the retention rate was improved. The degree of improvement in retention rate was 125%.

Example 9

The protein-adsorbing porous membrane was obtained by a graft reaction using the hollow fiber porous membrane made of polyethylene manufactured in Manufacturing Example 1 as a substrate. The graft reaction followed Manufacturing Example 2 except that the mixing ratio of glycidyl methacrylate (GMA):methanol in the reaction liquid was 2.3 parts by mass:97.7 parts by mass. The degree of grafting and ligand conversion rate of the obtained protein-adsorbing porous membrane was 32% and 96%, respectively. In addition, the outer diameter was 3.3 mm, and the inner diameter was 2.0 mm.

Three of the obtained protein-adsorbing porous membranes were taken, and modules (9A, 9B, and 9C) were molded as in Manufacturing Example 3.

For the module 9A, according to Evaluation Example 1, measurement was carried out and the degree of multilayering was calculated. The degree of multilayering was 2.3.

For the module 9B, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Example 5. (In other words, in the elution step, liquid passage in the opposite direction was performed.)

The dynamic adsorption capacity in the first adsorption was 21.1 mg/mL, and the dynamic adsorption capacity after 10 times of repetition was 20.7 mg/mL, and the retention rate was 98%.

Comparative Example 8

For the module 9C manufactured in Example 9, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Comparative Example 4. (In other words, in the elution step, all eluents were passed in the forward direction.)

The dynamic adsorption capacity in the first adsorption was 21.4 mg/mL, and the amount of dynamic adsorption after 10 times of repetition was 18.5 mg/mL, and the retention rate was 86.6%.

In the case of a degree of multilayering of 2.3, the retention rate in Comparative Example 8 was 77%, whereas in Example 9, the retention rate was 98% and the retention rate was improved. The degree of improvement in retention rate was 113%.

Example 10

The protein-adsorbing porous membrane was obtained by a graft reaction using the hollow fiber porous membrane made of polyethylene manufactured in Manufacturing Example 1 as a substrate. The graft reaction followed Manufacturing Example 2 except that the mixing ratio of glycidyl methacrylate (GMA):methanol in the reaction liquid was 1.0 parts by mass:99.0 parts by mass. The degree of grafting and ligand conversion rate of the obtained protein-adsorbing porous membrane was 14% and 97%, respectively. In addition, the outer diameter was 3.2 mm, and the inner diameter was 1.9 mm.

Three of the obtained protein-adsorbing porous membranes were taken, and modules (10A, 10B, and 10C) were molded as in Manufacturing Example 3.

For the module 10A, according to Evaluation Example 1, measurement was carried out and the degree of multilayering was calculated. The degree of multilayering was 1.6.

For the module 10B, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Example 5. (In other words, in the elution step, liquid passage in the opposite direction was performed.)

The dynamic adsorption capacity in the first adsorption was 10.4 mg/mL, and the dynamic adsorption capacity after 10 times of repetition was 10.1 mg/mL, and the retention rate was 97%.

Comparative Example 9

For the module 10C manufactured in Example 10, the evaluation of repeated dynamic adsorption capacity was carried out according to Evaluation Example 2. The type of the passed liquid, the order of liquid passage, the amount of liquid passage, and the direction of liquid passage in the evaluation were exactly the same as Comparative Example 4. (In other words, in the elution step, all eluents were passed in the forward direction.)

The dynamic adsorption capacity in the first adsorption was 10.6 mg/mL, and the amount of dynamic adsorption after 10 times of repetition was 9.9 mg/mL, and the retention rate was 93%.

In the case of a degree of multilayering of 1.6, the retention rate in Comparative Example 9 was 93%, whereas in Example 10, the retention rate was 97% and the retention rate was improved. The degree of improvement in retention rate was 104%.

Example 11

Nylon 6 (0.2 g), methylene chloride (10 g), and formic acid (0.1 g) were stirred at room temperature. Sodium t-butyl hypochlorite (2 g) was added thereto to allow the nylon 6 to dissolve. Methylene chloride was further added to the obtained solution so that the total mass was 100 g, to obtain an N-chloro-nylon 6 solution for coating layer formation.

A porous flat membrane comprising a cellulose derivative having a pore diameter of 0.45 μm and a membrane thickness of 0.15 mm (manufactured by Nihon Millipore K.K.) was immersed in the N-chloro-nylon 6 solution to allow the solution to impregnate into the porous portions. The excess solution was removed from the porous flat membrane impregnated with the solution. This membrane was first dried at room temperature, then further dried in a hot air circulating dryer at 80° C., and finally heated at 140° C. for 15 minutes to obtain a flat membrane-shaped substrate having a porous flat membrane of the cellulose derivative and a coating of N-chloro-nylon 6 covering its surface.

A sodium phosphate buffer (pH 7.5) having a composition of 5% of glycidyl methacrylate (GMA), 0.3% of Tween 80 (manufactured by KANTO CHEMICAL CO., INC.), and 0.1% of sodium dithionite was stirred well in a reaction container. The above flat membrane-shaped substrate was introduced into this sodium phosphate buffer to perform a graft polymerization reaction at room temperature for 12 minutes. The membrane after the reaction was washed with pure water and acetone in this order and then dried at 80° C. to obtain a grafted porous flat membrane having a graft chain formed by the graft polymerization of the GMA. The degree of grafting was 8%.

This degree of grafting was defined by graft chain weight to membrane weight before coating with N-chloro-nylon 6. In other words, the degree of grafting was calculated by the following formula (1)' obtained by modifying the above-described formula (1).

[Expression 9]

$$dg[\%] = \frac{W_1 - W_0'}{W_0} \times 100, \quad (1)$$

$W_0$: membrane weight before coating (g)
$W_0'$: substrate weight before graft chain introduction (g)
$W_1$: weight after graft polymerization (g)

An aqueous solution of diethylamine at a volume concentration of 50 was placed in a reaction container in which the grafted porous flat membrane was placed, circulated at 30° C. for 5 hours, and allowed to stand overnight, and then, the aqueous solution of diethylamine was discharged. Then, the porous flat membrane was sufficiently washed with water and dried to obtain a grafted porous flat membrane having a diethylamino group in a graft chain as a protein-adsorbing porous membrane. The ligand conversion rate obtained from the above-described formula (2) was 96%.

Using this porous flat membrane, flat membrane modules (11A, 11B, and 11C) were molded.

For the module 11A, according to Evaluation Example 1, measurement was carried out and the degree of multilayering was calculated. The degree of multilayering was 1.2.

For the module 11B, the evaluation of repeated dynamic adsorption capacity was carried out according to Evaluation Example 2. In other words, the evaluation flow rate was 5 MV/min in all steps. In the adsorption step, liquid passage was performed from the front surface to the back surface of the flat membrane, and then, as the washing step, the buffer was passed from the front surface to the back surface (the forward direction). Then, as the elution step, the salt buffer (the forward direction), the aqueous solution of sodium hydroxide (the opposite direction), and the salt buffer (the opposite direction) were passed. Here, the opposite direction means that liquid passage was performed from the back surface to the front surface of the flat membrane.

The dynamic adsorption capacity in the first adsorption was 7.7 mg/mL, and the dynamic adsorption capacity after 10 times of repetition was 7.5 mg/mL, and the retention rate was 97%.

Comparative Example 10

For the module 11C manufactured in Example 11, repeated dynamic adsorption capacity was evaluated as in the above Example 11. However, all the direction of liquid passage was the forward direction.

The dynamic adsorption capacity in the first adsorption was 8.4 mg/mL, and the amount of dynamic adsorption after 10 times of repetition was 7.9 mg/mL, and the retention rate was 94%.

In the case of a degree of multilayering of 1.2, the retention rate in Comparative Example 10 was 94%, whereas in Example 11, the retention rate was 97% and the retention rate was improved. The degree of improvement in retention rate was 103%.

Example 12

Three modules of the protein-adsorbing membrane porous membrane obtained in Manufacturing Examples 1 to 3 were subjected to treatment in which hot water at 90° C. was passed for 1 hour (modules 12A, 12B, and 12C).

For the module 12A, according to Evaluation Example 1, measurement was carried out and the degree of multilayering was calculated. The degree of multilayering was 4.7. For the module 12B, the evaluation of repeated dynamic adsorption capacity was carried out according to Evaluation Example 2. An adsorption step (30 mL of the buffer, 40 mL of the BSA solution) was performed in an internal pressure mode (liquid passage from the inside to the outside of the hollow portion), and then, as a washing step, 10 mL of the buffer was passed in the forward direction. Then, as an elution step, the salt buffer (15 mL, the forward direction), the aqueous solution of sodium hydroxide (20 mL, the opposite direction), and the salt buffer (20 mL, the opposite direction) were passed.

The dynamic adsorption capacity in the first adsorption was 58.5 mg/mL, and the dynamic adsorption capacity after 10 times of repetition was 56.7 mg/mL, and the retention rate was 97%.

Comparative Example 11

Evaluation was performed as in Example 5 except that for the module 12C manufactured in Example 12, all eluents were passed in the forward direction, the salt buffer (15 mL, the forward direction), the aqueous solution of sodium hydroxide (20 mL, the forward direction), and the salt buffer (20 mL, the forward direction), in the elution step.

The dynamic adsorption capacity in the first adsorption was 58.6 mg/mL, and the amount of dynamic adsorption after 10 times of repetition was 42.2 mg/mL, and the retention rate was 72%.

By the hot water treatment at 90° C., the degree of multilayering in Manufacturing Examples 1 to 3 increased from 4.2 to 4.7. In addition, the retention rate in Comparative Example 11 was 72%, whereas in Example 12, the retention rate was 97% and the retention rate was improved. The degree of improvement in retention rate was 135%.

The results of Example 12 and Comparative Example 11 are shown in Table 4.

TABLE 4

| | | | Example 12 | Comparative Example 11 |
|---|---|---|---|---|
| Treatment conditions | | | | |
| Step | Order of liquid passage | Type of passed liquid | Amount of liquid passage (Direction) | Amount of liquid passage (Direction) |
| Adsorption step | 1 | Buffer | 30 mL (Forward) | 30 mL (Forward) |
| | 2 | BSA solution | 40 mL (Forward) | 40 mL (Forward) |
| Washing step | 3 | Buffer | 10 mL (Forward) | 10 mL (Forward) |
| Elution step | 4 | Salt buffer | 15 mL (Forward) | 15 mL (Forward) |
| | 5 | Alkali | 20 mL (Opposite) | 20 mL (Forward) |
| | 6 | Salt buffer | 20 mL (Opposite) | 20 mL (Forward) |
| Results | | | | |
| | | | (Adsorption capacity unit: mg/mL) | |
| Number of times of repetition/times | | | Adsorption capacity (Retention rate) | Adsorption capacity (Retention rate) |
| 1 | | | 58.5   100 | 58.6   100 |
| 2 | | | 58.4   100 | 56.8   97 |
| 3 | | | 58.2   100 | 55.1   94 |
| 4 | | | 57.8   99 | 53.3   91 |
| 5 | | | 57.6   98 | 51.6   88 |
| 6 | | | 57.4   98 | 50.4   86 |
| 7 | | | 57.2   98 | 48.1   82 |
| 8 | | | 57.0   98 | 46.3   79 |
| 9 | | | 56.9   97 | 44.0   75 |
| 10 | | | 56.7   97 | 42.2   72 |
| Degree of improvement in retention rate | | | 135 | — |

This application is based on Japanese Patent Application No. 2011-217856 filed on Sep. 30, 2011, the content of which is incorporated herein by reference.

INDUSTRIAL APPLICABILITY

The present invention can provide an efficient method for purifying a protein using a protein-adsorbing porous membrane. The present invention has industrial applicability in the purification of a desired protein in efficiently mass-producing an antibody drug.

The invention claimed is:
1. A method for purifying a protein by a porous membrane having a substrate surface coated with a polymer having protein adsorption ability, comprising:
an adsorption step of passing a stock solution containing an adsorption target protein through a pore direction from one surface to another surface of the porous membrane to allow the polymer to adsorb the adsorption target protein; and
an elution step of passing an eluent through the porous membrane to allow the adsorption target protein that is adsorbed on the polymer to elute in the eluent,
wherein in the elution step, at least one eluent is passed in an opposite direction with respect to the pore direction of passage of the stock solution in the adsorption step;
wherein a degree of multilayering of the porous membrane is 1.1 or more, and the degree of multilayering is a value obtained by the following formula (3)

$$\text{degree of multilayering} = (\text{equilibrium adsorption capacity})/(\text{theoretical single-layer adsorption capacity}) \qquad (3)$$

where the equilibrium adsorption capacity is obtained by the following formula (4), when the stock solution comprising the adsorption target protein is passed through the porous membrane $$\text{equilibrium adsorption capacity } [g - \text{amount of adsorption}/g - \text{membrane}] = \frac{\int_0^{Q_e}(C_0 - C)dQ}{W} \qquad (4)$$

where $C_0$: concentration of protein in stock solution [g/L];
$C$: protein concentration in passed solution of stock solution [g/L];

Q: cumulative amount of passed solution of stock solution [L];

$Q_e$: amount of passed solution of stock solution when adsorption equilibrium is reached [L];

W: weight of protein-adsorbing porous membrane [g]; and the theoretical single-layer adsorption capacity is obtained by the following formula (5)

$$\text{theoretical single-layer adsorption capacity[g-amount of single-layer adsorption/g-membrane]} = (S_M/S_P)(M_r/N_A) \quad (5)$$

where $S_M$: specific surface area of protein-adsorbing porous membrane [m²/g];

$S_P$: area occupied by one protein molecule [m²];

$M_r$: molecular weight of BSA [g/mol]; and $N_A$: Avogadro's number [/mol].

2. The method for purifying a protein according to claim 1, wherein the eluent is selected from the group consisting of an aqueous solution comprising a salt, an aqueous solution whose pH is adjusted, water, an organic solvent, and a mixed solution thereof.

3. The method for purifying a protein according to claim 1, wherein in the elution step, the eluent is passed in a forward direction and an opposite direction with respect to the direction of the passage of the stock solution in the adsorption step.

4. The method for purifying a protein according to claim 1, wherein the polymer is grafted onto the substrate surface, and a degree of grafting of the polymer is 5% or more and 200% or less.

5. The method for purifying a protein according to claim 4, wherein the degree of grafting of the polymer is 30% or more and 90% or less.

6. The method for purifying a protein according to claim 1, wherein the porous membrane is an ion exchange membrane, and the eluent comprises an aqueous solution comprising a salt or an aqueous solution whose pH is adjusted.

7. The method for purifying a protein according to claim 6, wherein the porous membrane is a weakly basic anion exchange membrane or a weakly acidic cation exchange membrane, the elution step comprises the steps of:

passing an aqueous solution whose pH is adjusted to other than between an isoelectric point of the adsorption target protein and an isoelectric point of the porous membrane, and passing an aqueous solution comprising a salt, wherein in either of the steps, the aqueous solution whose pH is adjusted or the aqueous solution comprising a salt is passed in the opposite direction with respect to the direction of the passage of the stock solution in the adsorption step.

8. The method for purifying a protein according to claim 7, wherein in the step of passing an aqueous solution whose pH is adjusted and the step of passing an aqueous solution comprising a salt, respectively, the aqueous solution whose pH is adjusted and the aqueous solution comprising a salt are passed in the opposite direction with respect to the direction of the passage of the stock solution in the adsorption step.

9. The method for purifying a protein according to claim 6, wherein the porous membrane is a weakly basic anion exchange membrane or a weakly acidic cation exchange membrane, the elution step comprises a first step of passing an aqueous solution comprising a salt, a second step of passing an aqueous solution whose pH is adjusted to other than between an isoelectric point of the adsorption target protein and an isoelectric point of the porous membrane, and a third step of passing an aqueous solution comprising a salt, wherein in the first step, the aqueous solution comprising a salt is passed in the forward direction with respect to the direction of the passage of the stock solution in the adsorption step, and in the second step and the third step, respectively, the aqueous solution whose pH is adjusted and the aqueous solution comprising a salt are passed in the opposite direction with respect to the direction of the passage of the stock solution in the adsorption step.

10. The method for purifying a protein according to claim 1, wherein the eluent is adjusted at a stable pH for the adsorption target protein.

11. The method for purifying a protein according to claim 1, wherein the eluent is an aqueous solution comprising a neutral salt at 0.3 mol/L or more.

12. The method for purifying a protein according to claim 1, wherein the porous membrane is manufactured by performing treatment of heating to 50 to 110° C. in a state of being wetted with a liquid or a vapor.

13. The method for purifying a protein according to claim 2, wherein the eluent is an aqueous solution comprising a neutral salt at 0.3 mol/L or more.

14. The method of purifying a protein according to claim 1, wherein in the adsorption step, a stock solution containing an adsorption target protein having a pore diameter smaller than the pore diameter of the protein-adsorbing porous membrane and having a molecular size in which the adsorption target protein can pass through the pores is passed through the porous membrane.

15. The method of purifying a protein according to claim 1, wherein in the elution step, the liquid passage rate at which the eluent is passed through the protein-adsorbing porous membrane is in the range of 1 MV/min to 15 MV/min.

16. The method for purifying a protein according to claim 1, further comprising: a washing step of washing away components adhering to the protein-adsorbing porous membrane.

* * * * *